(12) United States Patent
Hong et al.

(10) Patent No.: US 11,875,701 B2
(45) Date of Patent: Jan. 16, 2024

(54) ADAPTIVE FORCE GUIDANCE SYSTEM FOR COMPUTER-ASSISTED LAPAROSCOPY TRAINING

(71) Applicant: Arizona Board of Regents on Behalf of the University of Arizona, Tucson, AZ (US)

(72) Inventors: Minsik Hong, Tucson, AZ (US); Jerzy W Rozenblit, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 114 days.

(21) Appl. No.: 17/520,852

(22) Filed: Nov. 8, 2021

(65) Prior Publication Data

US 2022/0148458 A1 May 12, 2022

Related U.S. Application Data

(60) Provisional application No. 63/110,549, filed on Nov. 6, 2020.

(51) Int. Cl.
*G16H 70/20* (2018.01)
*G09B 23/28* (2006.01)
*G09B 19/00* (2006.01)
*G16H 40/63* (2018.01)

(52) U.S. Cl.
CPC ......... *G09B 23/285* (2013.01); *G09B 19/003* (2013.01); *G16H 40/63* (2018.01); *G16H 70/20* (2018.01)

(58) Field of Classification Search
CPC .... G09B 23/285; G09B 19/003; G16H 40/63; G16H 70/20
See application file for complete search history.

(56) References Cited

U.S. PATENT DOCUMENTS

2019/0104919 A1* 4/2019 Shelton, IV ........... A61B 34/37

* cited by examiner

*Primary Examiner* — Robert P Bullington
(74) *Attorney, Agent, or Firm* — Stuart H. Mayer; Kaplan, Breyer, Schwarz LLP

(57) ABSTRACT

An adaptive force guidance system for laparoscopic surgery skills training includes self-adjusting fuzzy sliding mode controllers and switching mode controllers to provide proper force feedback. Using virtual fixtures, the system restrictS motions and/or guide a trainee to navigate a surgical instrument in a 3D space in a manner that mimics a human instructor who would teach trainees by holding their hands. The self-adjusting controllers incorporate human factors such as different force sensitivity and proficiency level.

12 Claims, 30 Drawing Sheets

HANDS-ON INTERFACE | HARDWARE CONFIGURATION | SOFTWARE MODULES

- TASK GENERATOR
- PATH GENERATOR
- ACTUATOR CONTROLLERS
- AR RENDERER
- PERFORMANCE EVALUATOR

| | RIGHT | |
|---|---|---|
| MET/4 | GOAL | ACTUAL |
| COMPLETION TIME (S) | 27.71 | 29.55 |
| IDLE TIME (<0.3cm/s) (s) | 2.77 | 4.95 |
| PATH LENGTH (cm) | 34.64 | 41.83 |
| AVG.SPEED (cm/1) | 1.50 | 1.39 |
| MAX.SPEED (cm/1) | 3.00 | 0.94 |
| AVG. DEVIATION (cm) | 0.50 | 0.29 |
| MAX. DEVIATION (cm) | 1.00 | 0.58 |

THIS IS YOUR PERFORMANCE

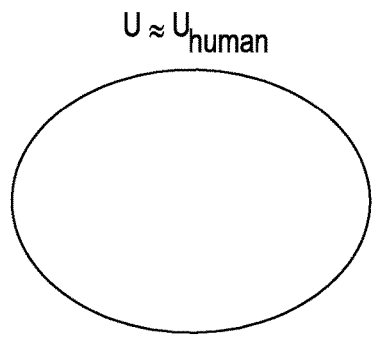
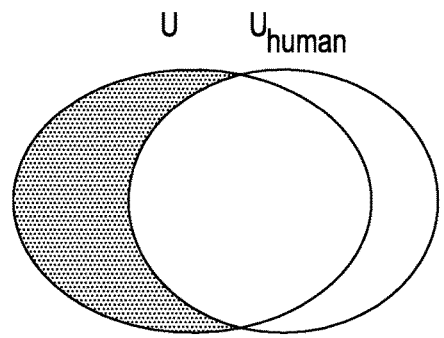
FIG. 16A                    FIG. 16B
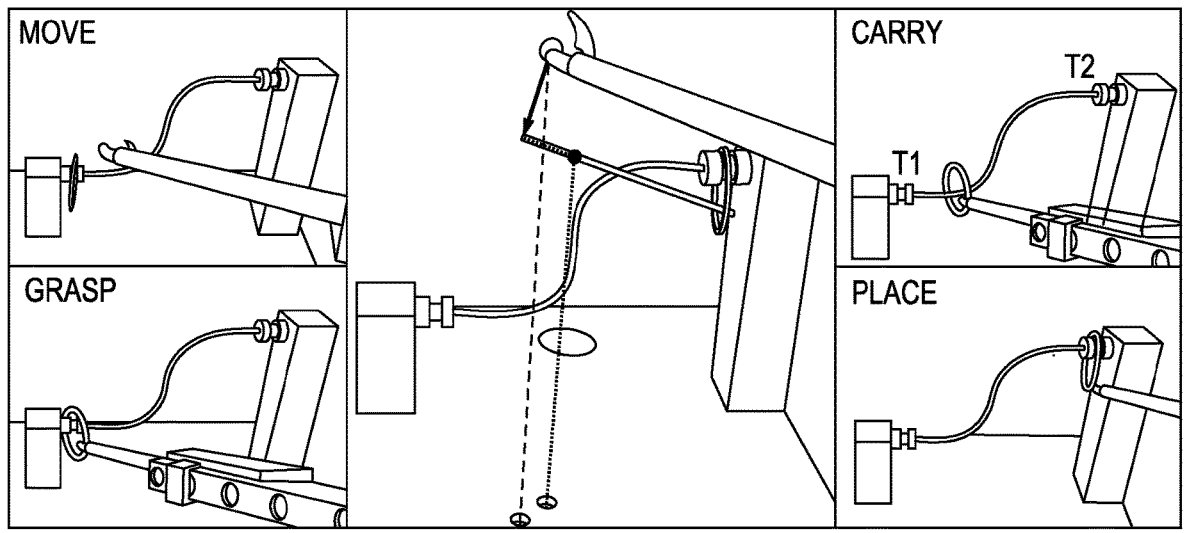
FIG. 17

ADAPTIVE FORCE GUIDANCE SYSTEM FOR COMPUTER-ASSISTED LAPAROSCOPY TRAINING

GOVERNMENT FUNDING

This invention was made with government support under Grant No. 1622589, awarded by National Science Foundation. The government has certain rights in the invention.

BACKGROUND

Laparoscopy, also known as minimally invasive surgery, reduces patients' recovery time, minimizes blood loss, and results in less post-operative pain when it is performed by an expert surgeon. In a typical procedure a patient's abdomen is insufflated, long, thin instruments and an endoscope are inserted through 3-10 mm incisions, and the three-dimensional (3D) operating field is observed on a two dimensional (2D) display. Compared to a traditional open surgery, this surgical procedure requires specialized training due to the lack of depth perception, hand-eye coordination problems, and restricted field of view. The Society of American Gastrointestinal and Endoscopic Surgeons (SAGES) in the United States designed the Fundamentals of Laparoscopic Surgery (FLS) certification program to provide a well-defined set of training tasks. This program consists of an instructive module to teach basic knowledge and a hands-on exam to evaluate trainees' surgical skills. A trainee must complete each task within a maximum time limit and meet a set of predetermined requirements (e.g., accuracy in executing a task). The tasks are performed in a non-patient based setting, on relatively simple trainers that use real surgical instruments and a simple camera setup.

Surgical training systems such as for laparoscopic surgery skills training may use a hands-on human machine interface in which a trainee uses a tool such as a surgical instrument to perform tasks. The training system shares control of the surgical instrument to assist the trainee in skills practice and acquisition.

A Computer-Assisted Surgical Trainer (CAST) has been developed which incorporates key features from both simple training devices and Virtual Reality Simulators. The CAST system is described in J. W. Rozenblit et al., "The Computer Assisted Surgical Trainer: Design, Models, and Implementation," in *Proceedings of the* 2014 *Summer Simulation Multiconference,* 2014, pp. 211-220. CAST provides not only realistic training environments such as 3D printed organ models, or setups such as the peg board for an FLS task but it also incorporates force-based and augmented reality (AR) guidance to assist trainees in learning how to execute surgical movements in a manner a human instructor would teach a trainee. The system has a module to generate sophisticated, quantitative and qualitative assessment metrics. Its hardware architecture consists of two mechanical fixtures which hold actual surgical instruments, a web camera to imitate an endoscope, an exchangeable cassette to support a variety of practice scenarios, motors to provide force guidance, and electronics to support control, sensing, and data collection.

Force guidance is widely used in prototypes for robotic surgery, tele-operation platforms, driver support systems, rehabilitation devices, handwriting assistance systems, and cooperative systems. Two types of human-machine interfaces—tele-operated and hand-on—are typically employed in such systems. The tele-operated devices generally consist of master and slave devices. A human operator manipulates the master device to control the slave device (e.g., a surgical robot). Unlike in the tele-operated devices, the hand-on devices share an actual tool (e.g., surgical instruments) with a human operator while performing tasks.

SUMMARY

Described herein is an adaptive force guidance system for laparoscopic surgery skills training. In some embodiments the system includes self-adjusting fuzzy sliding mode controllers and switching mode controllers to provide proper force feedback. Using virtual fixtures, the system can restrict motions and/or guide a trainee to navigate a surgical instrument in a 3D space in a manner that mimics a human instructor who would teach trainees by holding their hands. The self-adjusting controllers can incorporate human factors such as different force sensitivity and proficiency level. In some cases the system can be implemented and evaluated using the aforementioned Computer-Assisted Surgical Trainer (CAST).

In accordance with one aspect of the subject matter described herein, an adaptive force guidance system for surgical training includes a hands-on physical interface. The hands-on physical interface includes a fixture supporting an actuator-controllable surgical instrument for performing a surgical training task on a physical reality training arrangement using the surgical instrument. The hands-on physical interface further includes at least one sensor for receiving task performance data. In addition, the system includes a processor that is configured to generate or acquire a training task that includes a sequence of actions to be performed by a user of the surgical instrument for performing a task on the physical reality training arrangement. Each of the actions is associated with guidance geometry specifying a recommended path to be traversed to perform the respective action. While each action is being performed by the user of the surgical instrument as part of the training task, task performance data is received. The task performance data reflects an amount by which the action being performed by the user causes a deviation from the recommended path. While each action is being performed by the user of the surgical instrument, an adaptive feedback force is caused to be applied to the surgical instrument based at least in part on the received task performance data. The adaptive feedback force causes a reduction in the deviation from the recommended path.

In accordance with one aspect of the subject matter described herein, a magnitude of the adaptive feedback force that is applied is determined by a control gain, the processor being further configured to adjust the control gain based at least in part on a magnitude of the deviation.

In accordance with one aspect of the subject matter described herein, the processor is further configured to increase the magnitude of the control gain as a magnitude of the deviation increases and subsequently decrease the magnitude of the control gain as the user properly manipulates the surgical instrument in accordance with the guidance geometry.

In accordance with one aspect of the subject matter described herein, the processor is further configured to adjust the control gain based at least in part on an evaluation of past user performance data when performing previous actions in the training task such that the user has more control authority when the past user performance data indicates greater proficiency and has less control authority when the past user performance data indicates less proficiency.

In accordance with one aspect of the subject matter described herein, the processor is further configured to adjust the control gain based at least in part on an evaluation of historical training data of the user from previous training sessions such that the user has more control authority when the evaluation indicates greater proficiency and has less control authority when the evaluation indicates less proficiency.

In accordance with one aspect of the subject matter described herein, the processor is further configured to adjust a rate at which guidance intervention is provided based at least in part on an evaluation of past user performance data when performing previous actions in the training task such that the user has more control authority when the past user performance data indicates greater proficiency and has less control authority when the past user performance data indicates less proficiency.

In accordance with one aspect of the subject matter described herein, the guidance intervention that is provided is selected from the group comprising a frequency at which adaptive feedback force intervention is applied and a rate at which visual and/or audio guidance is provided.

In accordance with one aspect of the subject matter described herein, the task performance data further reflects one or more characteristics of the surgical instrument as the user is performing the action, the processor being further configured to adjust the control gain based at least in part on the one or more characteristics.

In accordance with one aspect of the subject matter described herein, the one or more characteristics are selected from the group comprising a direction in which a tip of the surgical instrument is moving while the user performs the action and a speed at which the surgical instrument is moving while performing the action.

In accordance with one aspect of the subject matter described herein, the adaptive feedback force includes an attractive and/or assistive adaptive feedback force.

In accordance with one aspect of the subject matter described herein, the processor is further configured to generate performance evaluation data assessing user proficiency at a completion of the training task.

This Summary is provided to introduce a selection of concepts in a simplified form. The concepts are further described in the Detailed Description section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

BRIEF DESCRIPTION OF THE DRAWINGS

FIGS. 16(A) and 16(B) show diagrams of the stability analysis for the human-in-the-loop.

FIG. 17 shows the four basic action of a wire transfer task.

DETAILED DESCRIPTION

System Overview

Current training devices generally do not offer force-based navigation using a hands-on interface with physical reality arrangements for laparoscopic surgery skills training (i.e., not robotic surgery training). Most such training devices use virtual reality environments with artificial haptic tactile feedback. Described herein are intelligent surgical training systems and methods that employ actual surgical instruments and realistic training scenarios and offers force-based guidance effectively by considering human factors such as different force sensitivity and proficiency. In particular, the systems and methods provide proficiency-based, active guidance through a hands-on interface to teach trainees like a human instructor for minimally invasive surgical skills training. The system includes hardware and software modules with physical reality training setups (e.g., 3D printed organ models). For hardware, there are actuators to provide force-based guidance, mechanical fixtures to install real surgical instruments and to connect the actuators and the surgical instruments, electronics components with sensors (e.g., encoders) to support actuator control and instrument tracking, a computing device (e.g., a PC) to run software modules, a camera interface (e.g., a web camera) to imitate an endoscope, and a display device (e.g., a monitor) to render visual guidance information with training scene as well as to play audio guidance information. For software, there are a task generator to provide the entire training steps of surgical actions (e.g., move and carry), a path generator to provide a recommended instrument trajectory, actuator controllers to manage force-based guidance, an augmented reality (AR) renderer to display visual guidance information, and a performance evaluator to adjust guidance schemes by assessing proficiency.

Given a specific training scenario, the system provides adaptive force guidance based on live performance evaluation. The system's intervention (i.e., force feedback) will be minimized for a trainee to complete a training exercise by himself/herself if the trainee performs well. Conversely, the system's intervention will be more "aggressive" to teach a trainee through forces exerted on the surgical instruments.

Figure 1:
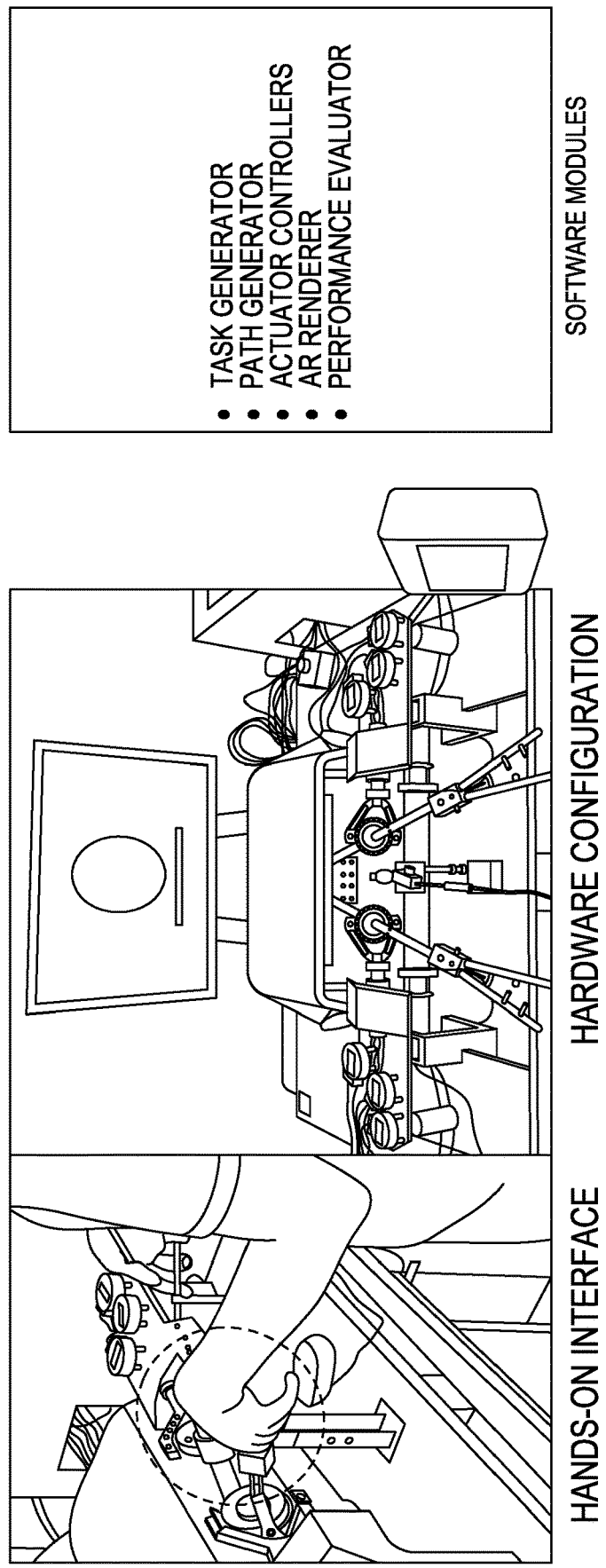
FIG. 1 shows an example of the overall adaptive force guide system configuration, including the hands-on interface (left panel) and the hardware (right panel).

FIG. 1 shows an example of the overall adaptive force guide system configuration, including the hands-on interface (left panel) and the hardware (right panel).

Figure 2:
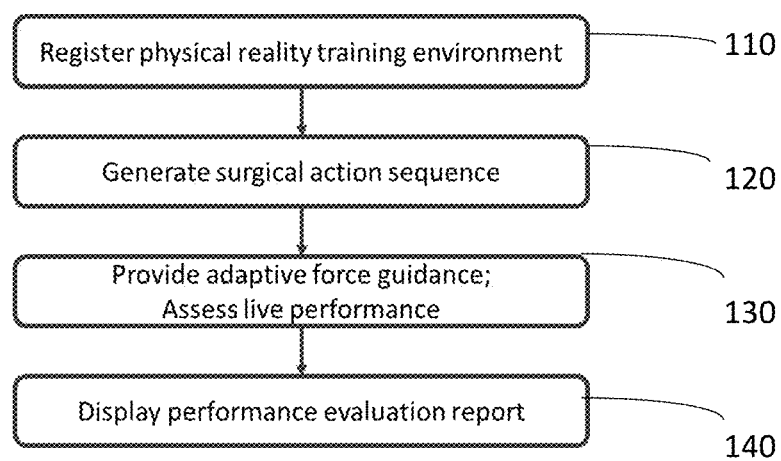
FIG. 2 is a flowchart of the overall operation of the adaptive force guidance system.
Figure 3B:
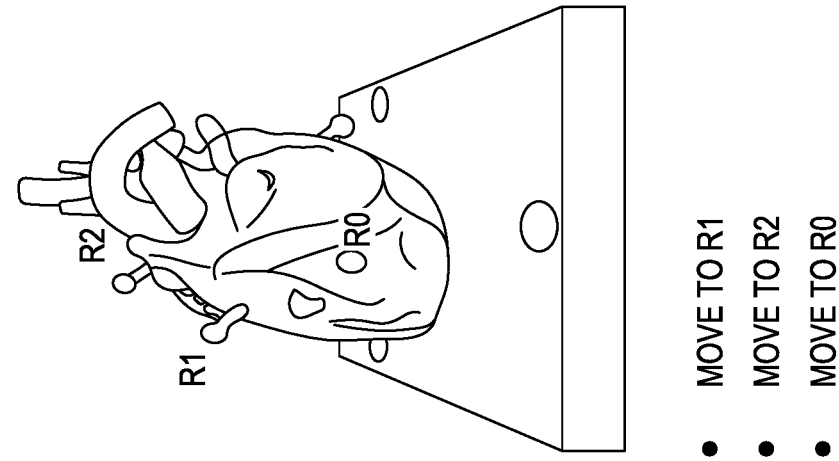
FIG. 3(B) shows an example of surgical actions performed on a 3D printed heart.
Figure 3A:
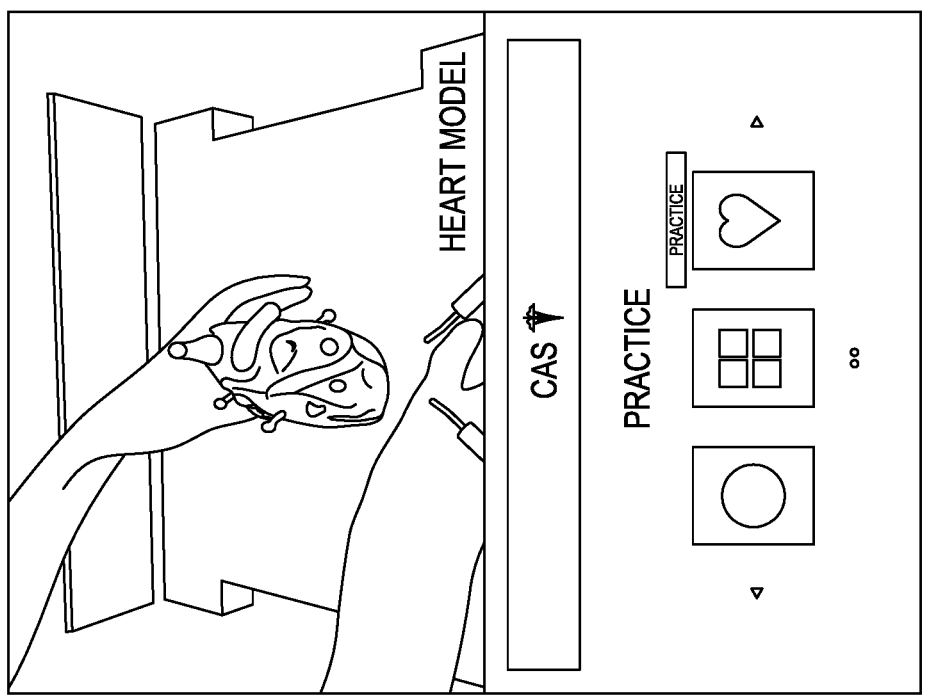
FIG. 3(A) shows an example of a training arrangement.

FIG. 2 is a flowchart of the overall operation of the adaptive force guidance system. In step 110, a physical reality (PR) environment is registered for the system to acquire details of the training setup such as the location of the environment, information concerning dynamic objects, available actions, and so on. A task description scheme may be employed for this purpose such as JSON (JavaScript Object Notation), for instance. By way of example, after a trainee arranges a training setup (e.g., a 3D printed heart such as shown in FIG. 3(A)), he/she clicks the corresponding button for the system to obtain the target task (e.g., instrument navigation such as "move an instrument to a specific location") by loading the JSON file (which contains, e.g., the location of the heart with respect to the world coordinate and the set of target locations for the move action).

In step 120, the task generator creates a set of surgical actions to represent a training exercise. By way of example, given the 3D printed heart shown in FIG. 3(A), the task generator randomly selects multiple target locations which are defined in the JSON file and configures the set of actions ("move to R1 using the right instrument", "move to L1 using the left instrument", "move to R7 using the right instrument", . . . ). FIG. 3(B) illustrates the surgical action sequence for the 3D printed heart of FIG. 3(A).

Figure 3C:
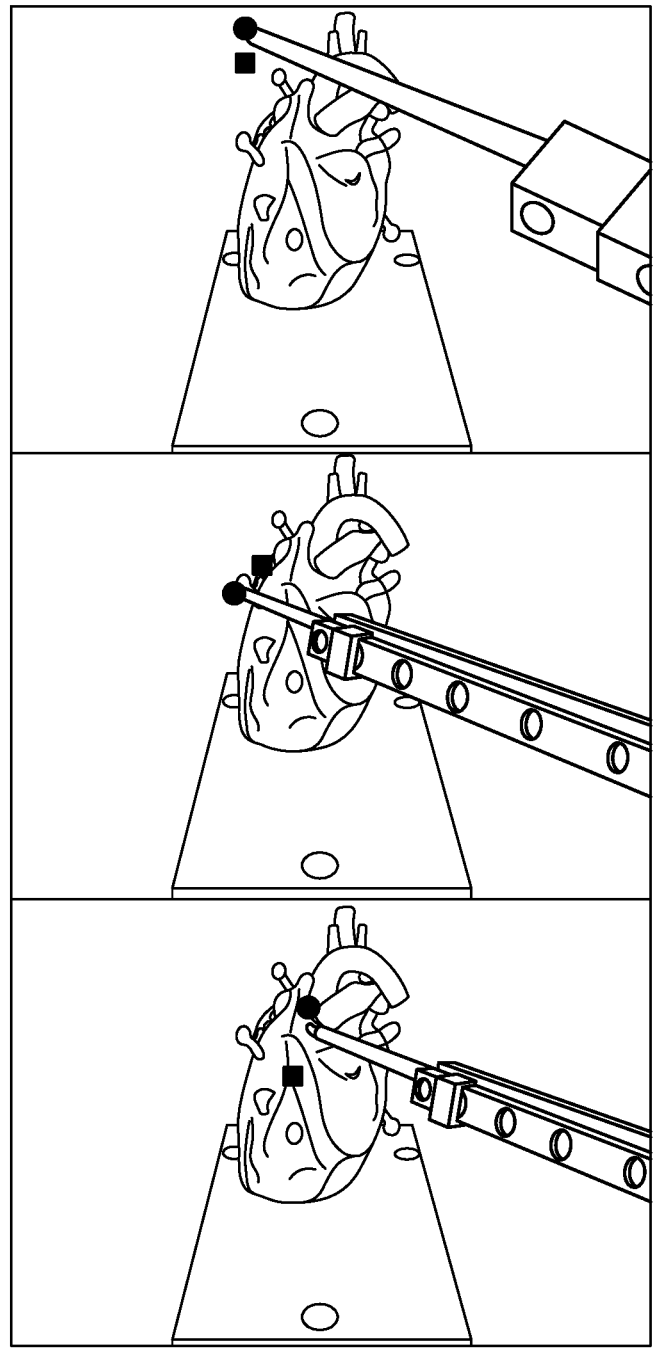
FIG. 3(C) shows an example of force feedback provided during a training exercise session.

During a training exercise session, force feedback is provided in step 130 of FIG. 2 as needed based on the live performance evaluation. This is illustrated in FIG. 3(C) for the example of the 3D printed heart. Details of this process will be described below in connection with FIG. 4. Also, assessment data such as instrument movements and dynamic objects' states are collected for the final performance evaluation.

Figure 3D:
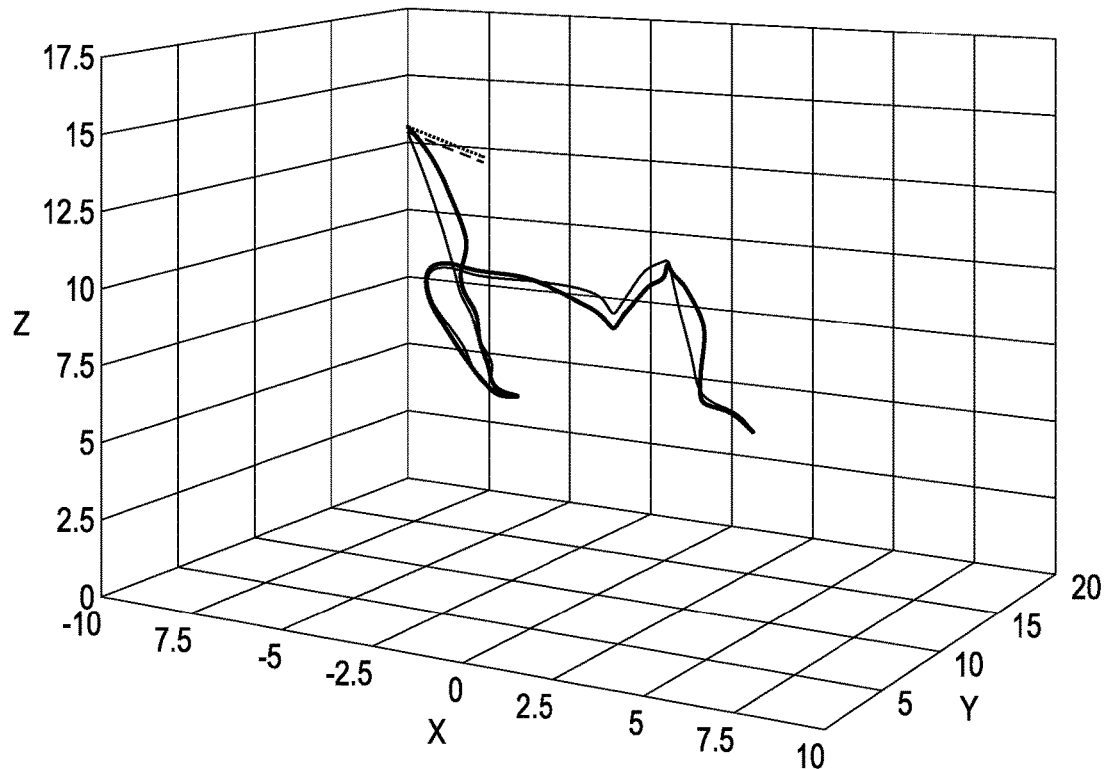
FIG. 3(d) shows an example of a performance evaluation report.

When a trainee terminates the exercise session, the performance evaluation report is displayed in step 140 of the flowchart in FIG. 2. An example of a performance evaluation report is shown in FIG. 3(D).

Figure 4:
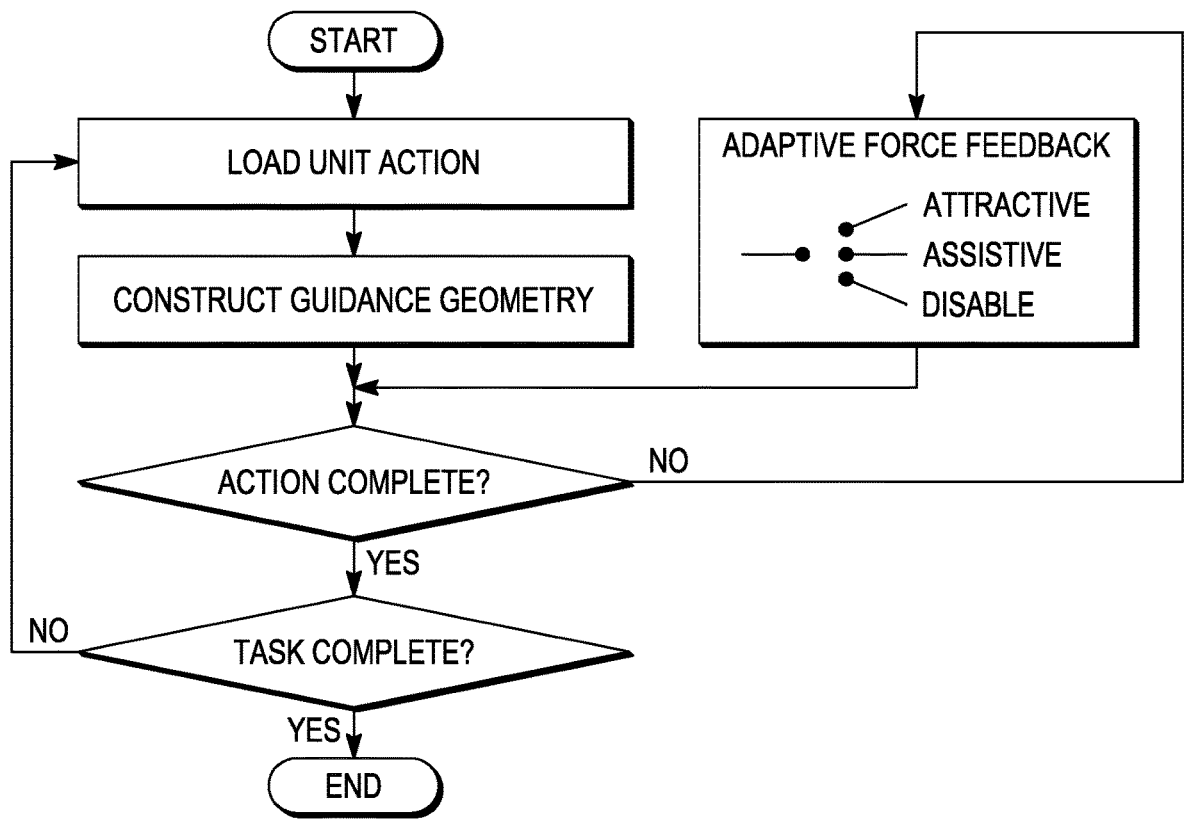
FIG. 4 is a flowchart illustrating one example of the force feedback process.

The adaptive force guidance system can provide both attractive (i.e., minimize deviations from a desired trajectory) and assistive (i.e., help a trainee traverse a desired trajectory) force feedback to a trainee who is performing a task, depending on the need to correct the trainee's instrument manipulation. FIG. 4 is a flowchart illustrating one example of the force feedback process. The process begins at step 210 and moves to step 220, where a unit action (e.g., move to R1) is loaded from the action sequence (e.g., move to R1; move to R2; move to R0). In step 230, the corresponding guidance geometry (e.g., a 3D tube) is constructed based on the instrument tip location and the computer-generated recommended path (e.g., collision-free and shortest path from the instrument tip to R1). Adaptive force feedback loop is activated while a trainee performs the unit action. Based on the live performance evaluation (e.g., amount of deviation from the recommended path, instrument tip movement direction, instrument tip speed), the proper force feedback is provided in step 250.

For example, if the instrument tip keeps deviating from the desired path (i.e., the tip is outside of the guidance geometry), a much stronger feedback force will be provided by adjusting the control gain. In this case, a trainee applies a stronger force that causes a deviation from the desired path. By increasing gain, the trainee can recognize force feedback so that he or she manipulates the instrument properly. When the trainee manipulates the instrument to return to the desired path, the amount of force will decrease rapidly for the trainee to have more control authority. Consider the case where the tip is inside of the guidance geometry. When a trainee has difficulties while performing the move action (e.g., due to depth perception issues), it is better to provide proper force for the trainee to traverse the desired path (i.e., the force feedback indicates the movement direction) by adjusting the control gain. Then, if the trainee keeps following the desired path well, with reasonable speed which is slightly faster than a reference speed, the controller for the assistive force will reduce the amount of force immediately for the trainee to have more control authority.

When the system recognizes a completion condition (e.g., the instrument tip and R1 are close to each other) of the unit action at decision step 240, it exits the force feedback loop and loads the next unit action (e.g., move to R2) as determined at decision step 260 or ends the process at step 270 if all actions have been performed and the task completed.

In one alternative implementation, the adaptive force guidance system can provide personalized guidance based on a training history given a specific training exercise. Force guidance parameters (e.g., control gains) may be recorded during the training session and processed to determine the recommended initial parameters for the individual trainee. In this case the system's intervention is adjusted according to the proficiency level. Compared to the adaptive force guidance system, this operation manages all the guidance schemes (e.g., visual, audio, and force). Each guidance scheme can be activated simultaneously or individually based on the user profile.

Figure 5:
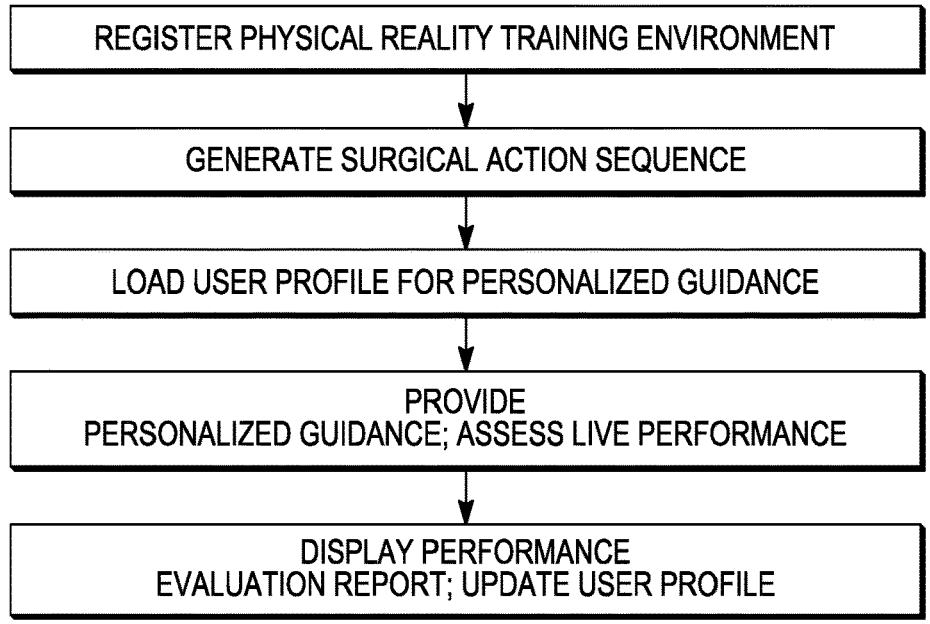
FIG. 5 is a flowchart illustrating one example of the force feedback process providing personalized guidance.

FIG. 5 is a flowchart illustrating one example of the force feedback process providing personalized guidance. The process begins at step 310, where a physical reality (PR) environment is registered for the system to acquire details of training. In step 320 the task generator creates a set of surgical actions to represent a training exercise. Next, in step 330 the system loads user profile data to provide personalized guidance. The user profile is updated based on the training history. Using user profile data, the guidance schemes are adjusted. For example, if the user profile indicates that a trainee is a novice, then the system may provide more active guidance information (e.g., issue interventions more frequently). On the other hand, if the user profile indicates that a trainee is somewhat of an expert according to the training history of the specific task, then interventions can be minimized to provide much more freedom for a trainee to complete this exercise by him or herself (e.g., allow a minor mistake while correcting a major mistake such as a large deviation). During a training exercise session, interventions are provided. The system can provide force, visual, and audio guidance in step 340 based on the live performance evaluation as well as the user profile. Also, assessment data such as instrument movements and dynamic objects' states are collected for the final performance evaluation. When a trainee terminates the exercise session, the performance evaluation report is displayed in step 350. The user profile data may be updated in this step as well.

In some embodiments two types of evaluation schemes may be used to configure a user profile given a specific training exercise. One evaluation scheme may be an objective evaluation and the other may be a subjective evaluation.

The objective evaluation may use metrics such as path length, completion time, idle time, amount of deviations, and average speed to assess a trainee's proficiency. The overall proficiency (which represents the overall training exercise performance) can be used to determine the baseline interventions. The objective evaluation scores are fed to a decision process to estimate the overall proficiency. Also, the system can use the itemized proficiency for the individual unit action. For instance, even though a given trainee's overall proficiency is intermediate, this trainee may receive stronger interventions for a specific unit action due to the itemized proficiency evaluation.

The subjective evaluation may use metrics (e.g., a questionnaire) to assess the usefulness of the individual guidance scheme. If a trainee keeps reporting that a specific guidance scheme is not helpful, the personalized guidance system can minimize or eliminate it.

Design of Force Guidance System

The adaptive force guidance system may employ a framework that uses virtual fixtures. Such virtual fixtures are described, for example in S. A. Bowyer, B. L. Davies, and F. Rodriguez Y Baena, "Active constraints/virtual fixtures: A survey," *IEEE Trans. Robot.*, vol. 30, no. 1, pp. 138-157, 2014. The following description details one specific implementation of the adaptive force guidance system using such fixtures.

a) Constraint Geometries

Forbidden region virtual fixtures (FRVFs) and guidance virtual fixtures (GVFs) are used for attractive force to minimize a deviation and assistive force to help a trainee traverse a desired path, respectively.

Figure 6A:
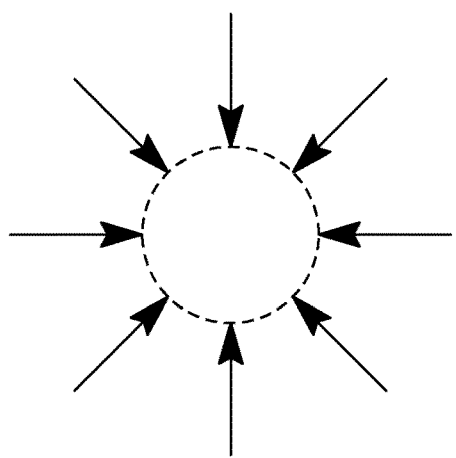
FIG. 6(A) shows a sphere that is used to generate a forbidden region virtual fixture (FRVF)

Given a target location ($p_{tgt} \in \mathbb{R}^3$), a sphere (FIG. 6(A)) is used to generate a FRVF. The target location represents the center of the sphere. By defining the radius with the center position, the sphere is generated. The outside of the sphere represents a forbidden region. An instrument tip can move freely inside the sphere. If the tool tip enters the forbidden region, the corresponding controller applies attractive force to minimize the deviation from the center of the sphere.

Figure 6B:
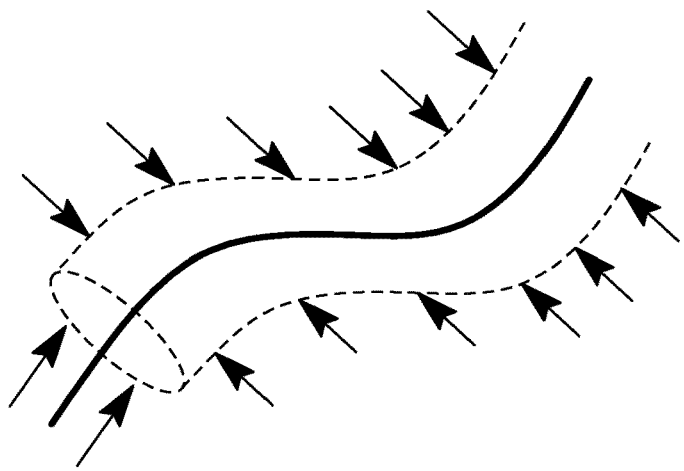
FIG. 6(B) shows a virtual tube that is used to generate a FRVF and FIG. 6(C) shows a virtual tube that is used to generate a guidance virtual fixture (GVF).

Given a desired path (P={$p_1, \ldots, p_m$}, where $p_i \in \mathbb{R}^3$, i=1, ..., m) expressed by a set of line segments that consists of three-dimensional discrete points, a virtual tube (FIG. 6(B)) is defined by a tube axis and a tube radius. The desired path is used to represent the tube axis. The role of the virtual tube is the same with the sphere: if a tool tip is inside the tube, the tip can move freely. Otherwise, attractive force is applied to minimize the deviation from the tube axis.

Figure 6C:
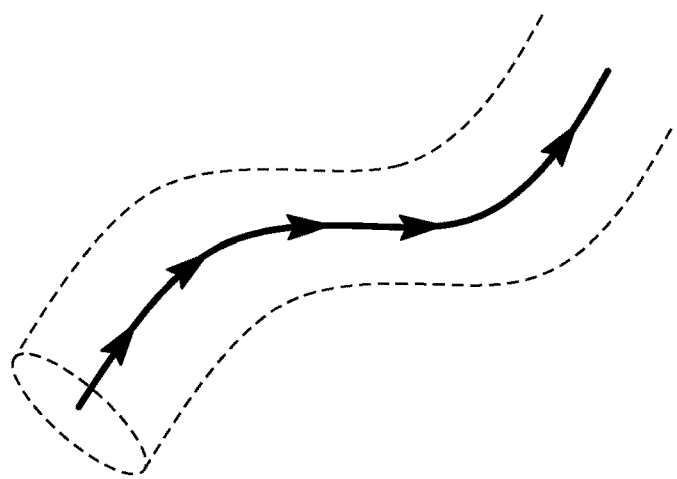

The virtual tube geometry is also used to design a GVF as shown in FIG. 6(C). The assistive force is generated inside the tube. If the tool tip is outside of the tube boundaries, the assistive force should be adjusted to prevent a wrong move.

b) Controllers

The control objective is that the system output x follows the given reference input signal $x_d$. The tracking error e and its change of error $\Delta e$ are defined as follows:

$$e(k) = x_d(k) - x(k),$$

$$\Delta e(k) = e(k) - e(k-1),$$

where k represents a discrete time domain. The signed distance $d_s$ is defined as follows: $d_s(k) = s(k)/\sqrt{1+\lambda^2}$ where s is a switching line and $\lambda$ is a slope of the switching line s. The switching line is defined as $$s(k) = \lambda e(k) + \Delta e(k).$$

Consider a fuzzy sliding mode controller with a signed distance (Sd-FSMC). The control output Y and the signed distance $d_s$ have the following relationship: $Y(k) \propto d_s(k)$.

Two types of controllers to provide both attractive force and assistive force are designed based on the above equations.

2) PD-Like Fuzzy Sliding Mode Controller

Figure 7:
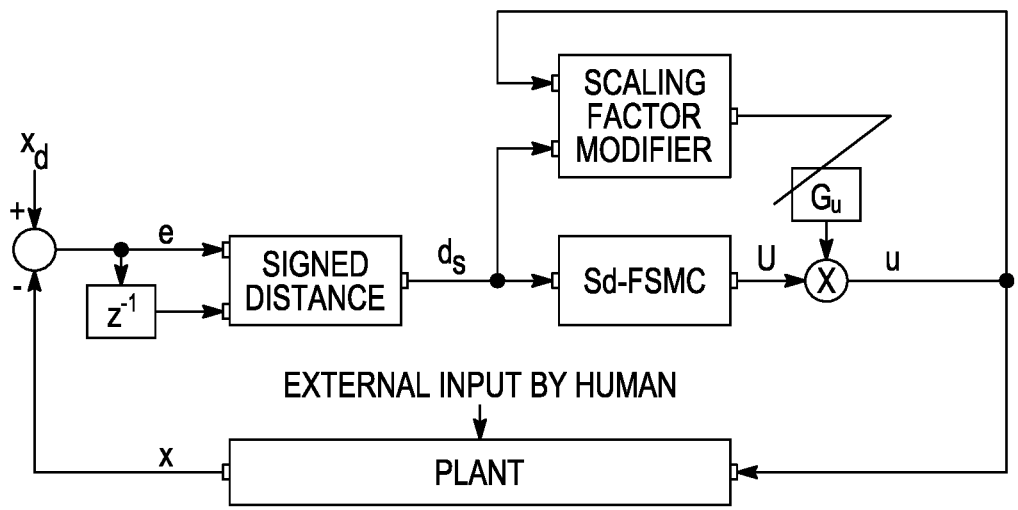
FIG. 7 shows a block diagram of one example of proportional and derivative (PD) like fuzzy sliding mode controller.

For force-based guidance systems, a simple proportional controller or a proportional and derivative (PD) controller has been widely used. Without adaptive features like adjusting control gains, it is challenging to take into account each individual's different force sensitivity. Inspired by several existing self-tuning fuzzy controllers, we designed a PD-like fuzzy sliding mode controller with a scaling factor modifier. A block diagram of an example of such a controller is illustrated in FIG. 7.

The PD-like fuzzy logic controller can be described as follows:

$$u(k)=G_u(k)\cdot U(k),$$

where u is the final control output, $G_u$ ($0<G_u<G_u^{max}$) is an output scaling factor calculated by the scaling factor modifier (SFM), and U ($-1\leq U\leq 1$) is the output of Sd-FSMC.

Fuzzy IF-THEN rules for Sd-FSMC are represented in the following form:

$R_{PD}^l$: If $d_s$ is $D_{PD}^l$, then U is $\overline{U}^l$, where $D_{PD}^l$ is a linguistic value to represent a signed distance, $\overline{U}^l$ is a singleton output value ($-1\leq\overline{U}^l\leq 1$), and l is a rule number. The controller output U is obtained from the following equation by using a singleton fuzzifier, a product inference engine, and a center average defuzzifier.

$$U=\Sigma_{l=1}^n \mu_{PD}^l(d_s)\overline{U}^l/\Sigma_{l=1}^n \mu_{PD}^l(d_s),$$

where $\mu_{PD}^l(d_s)$ is the degree of the fuzzy membership function and n is the number of rules.

Figure 8:
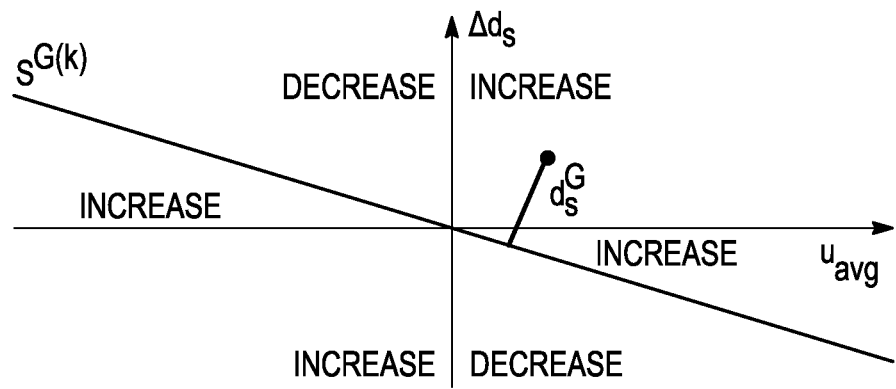
FIG. 8 shows an example of heuristic rules that may be used to adjust the output scaling factor modifier.

The output scaling factor is updated using the average control output ($u_{avg}$) and $\Delta d_s(k)=d_s(k)-d_s(k-1)$. Simple heuristic rules are designed by introducing an additional switching line $s^G$.

$$s^G(k)=\Delta d_s(k)+\lambda^G u_{avg}(k),$$

where $\lambda^G$ is a slope of the switching line $s^G$ and $u_{avg}(k)=(u(k-1)+u(k-2))/2$. The heuristic rules to adjust the output scaling factor $G_u$ are illustrated in FIG. 8. The rules are determined by estimating a human operator's behavior. For instance, when $u_{avg}$ is positive, the expectation of the tip movement is decreasing the absolute value of $d_s$ on approach to the switching line s. Unlike the expectation, if the tip keeps deviating from the switching line s (i.e., $\Delta d_s$ is positive as shown in FIG. 8), much stronger feedback force will be required so that the scaling factor $G_u$ should be increased (i.e., a human operator applies much stronger force that causes a deviation from the desired path. By increasing gain, the operator can recognize force feedback so that he or she moves the instrument properly.). Also, if the tool tip moves toward the correct direction (② and ⑤ in FIG. 8), the scaling factor $G_u$ should be decreased. The heuristic rules are summarized as follows:

If $u_{avg}>0$ and $d_s^G>0$, then increase $G_u$.
If $u_{avg}<0$ and $d_s^G<0$, then increase $G_u$.
If $u_{avg}>0$ and $d_s^G<0$, then decrease $G_u$.
If $u_{avg}<0$ and $d_s^G>0$, then decrease $G_u$.
If $u_{avg}=0$ or $d_s^G=0$, then keep $G_u$.

For this operation, the increasing or decreasing factor ($h^G$) is calculated based on a signed distance $d_s^G=s^G/\sqrt{1+(\lambda^G)^2}$. The final $G_u$ is calculated using the following form $$G_u(k)=\begin{cases} G_u(k-1)+\alpha^G h^G(k), & \text{if } h^G(k)\geq 0 \\ \exp(\beta^G h^G(k))\cdot G_u(k-1), & \text{otherwise} \end{cases},$$

where $\alpha^G$ ($\alpha^G>0$) is an additive increase gain, $\beta^G$ ($\beta^G>0$) is a multiplicative decrease gain, and $h^G$ is defined as follows:

$$h^G(k)=\begin{cases} d_s^G(k)/\omega, & u_{avg}>0 \\ 0, & u_{avg}=0 \\ -d_s^G(k)/\omega, & u_{avg}<0 \end{cases},$$

where ω (ω>0) is a scaling weight. To adjust the output scaling factor effectively, the Additive Increase and Multiplicative Decrease (AIMD) algorithm is used. (AIMD has been used effectively for network congestion control and it guarantees convergence) For instance, if a tool tip moves toward a forbidden region, the control gain should be increased gradually to generate strong force. However, if the tip moves from the forbidden region to a desired path, the control gain will be reduced rapidly in order to provide much more control authority to a trainee.

3) PI-Like Fuzzy Sliding Mode Controller

Figure 9:
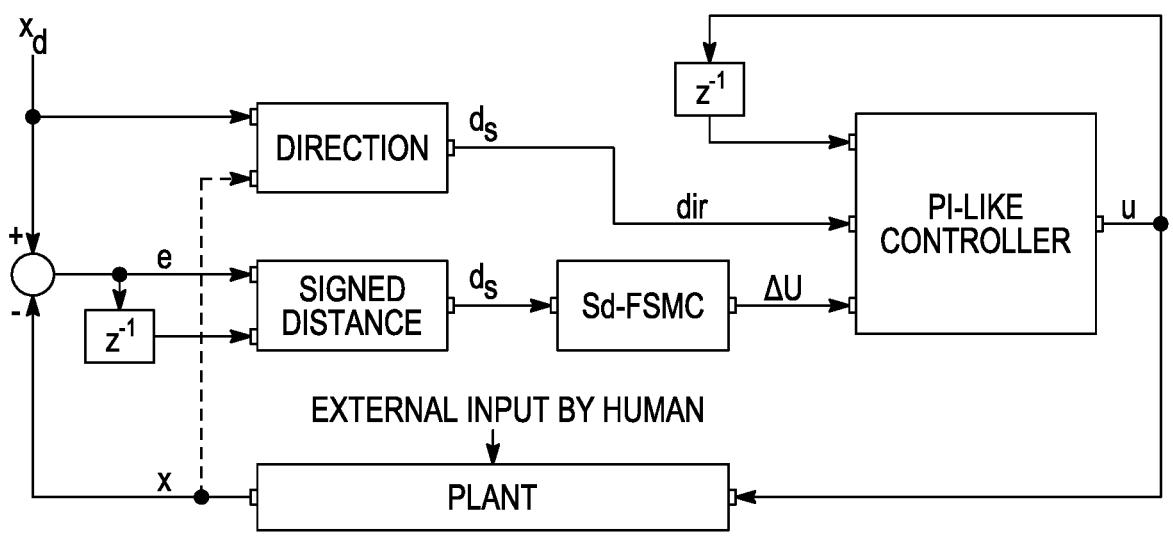
FIG. 9 shows a block diagram of one example of proportional and integral (PI) like fuzzy sliding mode controller.

The basic formula of the proportional and integral (PI) type fuzzy logic controller (FLC) is as follows:

$$u(k)=u(k-1)+\Delta u(k),$$

where $\Delta u$ is the incremental change of the control output that is determined by fuzzy IF-THEN rules. Using this controller, we can take into account different force sensitivity because the PI-type FLC adjusts control output gradually based on the fuzzy rules. However, in order to provide more control authority effectively to a trainee when the trainee performs well, a modification is required. For instance, consider a trajectory following task. When a trainee has difficulties while performing, it is better to provide proper force guidance by using incremental change. However, if the trainee keeps following the trajectory well with reasonable speed which is slightly faster than a recommended speed, the PI-type controller may sometimes provide resistance force because it decreases the absolute value of output u and finally changes the sign of the control output to reduce the tool tip speed. Instead of applying resistance force, the PI-like controller just reduces the absolute value of control output (i.e., $|u(k)|\to 0$) so that the trainee has more control authority. A block diagram of an example of such a controller is presented in FIG. 9.

The PI-like fuzzy logic controller can be described as follows:

$$u(k)=\begin{cases} u(k-1)+\kappa\cdot\eta(k)\cdot dir(k), & \eta(k)\geq 0 \\ \exp(\gamma\eta(k))\cdot u(k-1), & \eta(k)<0 \end{cases},$$

where dir(k) is a unit vector to represent a direction toward a reference, κ (κ>0) is an additive increase gain, γ (γ>0) is a multiplicative decrease gain, and $\eta(k)=\Delta U(k)\cdot dir(k)$. $\Delta U$ ($-1\leq\Delta U\leq 1$) is calculated by using Sd-FSMC. The direction vector and the multiplicative decrease are used to avoid generating resistance force. The direction vector should be updated whenever $x_d$ is changed. For instance, if $x_d(k)=5$ for k<5 and x(0)=0, then dir(k)=1 for k<5. The direction vector will be updated as dir(k)=−1 for k≥5 if $x_d(k)=0$ for k≥5 and x(5)=4.5.

The corresponding fuzzy IF-THEN rules are represented as follows:

$R_{PI}^l$: If $d_s$ is $D_{PI}^l$, then $\Delta U$ is $\Delta\overline{U}^l$, where $D_{PI}^l$ is a linguistic value to represent a signed distance, $\Delta\overline{U}^l$ is a singleton output value ($-1\leq\Delta\overline{U}^l\leq 1$), and l is a rule number. The control output $\Delta U$ is obtained from the following equation by using a singleton fuzzifier, a product inference engine, and a center average defuzzifier.

$$\Delta U=\Sigma_{l=1}^n \mu_{PI}^l(d_s)\Delta\overline{U}^l/\Sigma_{l=1}^n \mu_{PI}^l(d_s),$$

where $\mu_{PI}^l(d_s)$ is the degree of the fuzzy membership function and n is the number of rules.

4) MD-Type Controller

This is a simple controller to decrease the absolute value of output rapidly. This controller can be expressed as follows:

$$u(k)=\beta_{MD}u(k-1),$$

where $\beta_{MD}$ ($0<\beta_{MD}<1$) is a multiplicative decrease gain.

Illustrative Implementation of Force Guidance System

In the adaptive force guidance system may use two mechanical fixtures and each fixture has a gimbal that allows four degrees of freedom (4 DOF: yaw, pitch, roll, and insertion). A trocar is used to insert various surgical instruments into a human body while performing laparoscopic surgery. The gimbal not only imitates the trocar's functionality but it also facilitates the expression of real instrument movements. Currently, we use three motors to control yaw, pitch, and insertion axis. However, four encoders are used to monitor 4 DOF movement.

The following notations are used to implement the force guidance system.

Instrument tip position: $p_{tip}(k) \in \mathbb{R}^3$
Nearest point from $p_{tip}$ on a path: $p_{near}(k) \in \mathbb{R}^3$
Path direction vector at $p^{near}$: $v^{ref}(k)$
The deviation from the path: $d_{dev}(k)=\|v_{dev}(k)\|$ where $v_{dev}(k)=p_{tip}(k)-p^{near}(k)$

A. Controllers for Attractive Force

The objective of these controllers is to provide force feedback for a trainee to minimize a deviation from a reference point or a desired path. To accomplish this objective, position controllers are implemented. In order to control motors directly, the corresponding encoder counter values ($q \in \mathbb{N}^4$) given a 3D position ($p \in \mathbb{R}^3$) are used. q is calculated using the equation below.

$$q=g^{-1}(p|\Theta),$$

where $q=(q^{yaw}, q^{ins}, q^{pit}, q^{rol})$, $g^{-1}$ is a function to represent the relationship, and $\Theta$ is a set of parameters.

1) Reference Generation

The control reference input $q_{attr}$ is obtained from a reference position $p_{attr}$ using a specific geometry that constructs a FRVF. For attractive force, a sphere or a virtual tube is used as constraint geometry.

Given a target point ($p_{tgt}$) as the center of a sphere with a radius (r), the reference position $p_{attr}$ is defined as follows:

$$p_{attr}(k) = \begin{cases} p_{near}(k) + r \cdot (v_{dev}(k))/d_{dev}(k), & d_{dev} \geq r \\ p_{tip}(k), & d_{dev} < r \end{cases},$$

where $p_{near}(k)=p_{tgt}(k)$. The expected control actions are as follows:

$$\text{ctrl\_action} = \begin{cases} \text{Free}, & d_{dev} < r \\ \text{Guide}, & d_{dev} \geq r \end{cases},$$

where Free indicates that a human trainee has full control authority and Guide denotes that a controller restricts a trainee's motion.

To use the virtual tube geometry, the following additional terms are defined as follows:

Directional path: $P=\{p_1, \ldots, p_m\}$ where $p_i \in \mathbb{R}^3$, $i=1, \ldots, m$, $p_1$ is the initial point, and $p_m$ is the goal point Modified nearest point: $\tilde{p}_{near}(k) \in \mathbb{R}^3$ $p_{near}(0)=\tilde{p}_{near}(0)=p_1$ Distance w: $w(k)=\|v_{near}(k)\|$ where $v_{near}(k)=p_{near}(k)-\tilde{p}_{near}(k)$ and the next modified nearest point $\tilde{p}_{near}(k+1)$ is updated based on $p_{tip}(k)$, $p_{near}(k)$, and $\tilde{p}_{near}(k)$.

Figure 10:
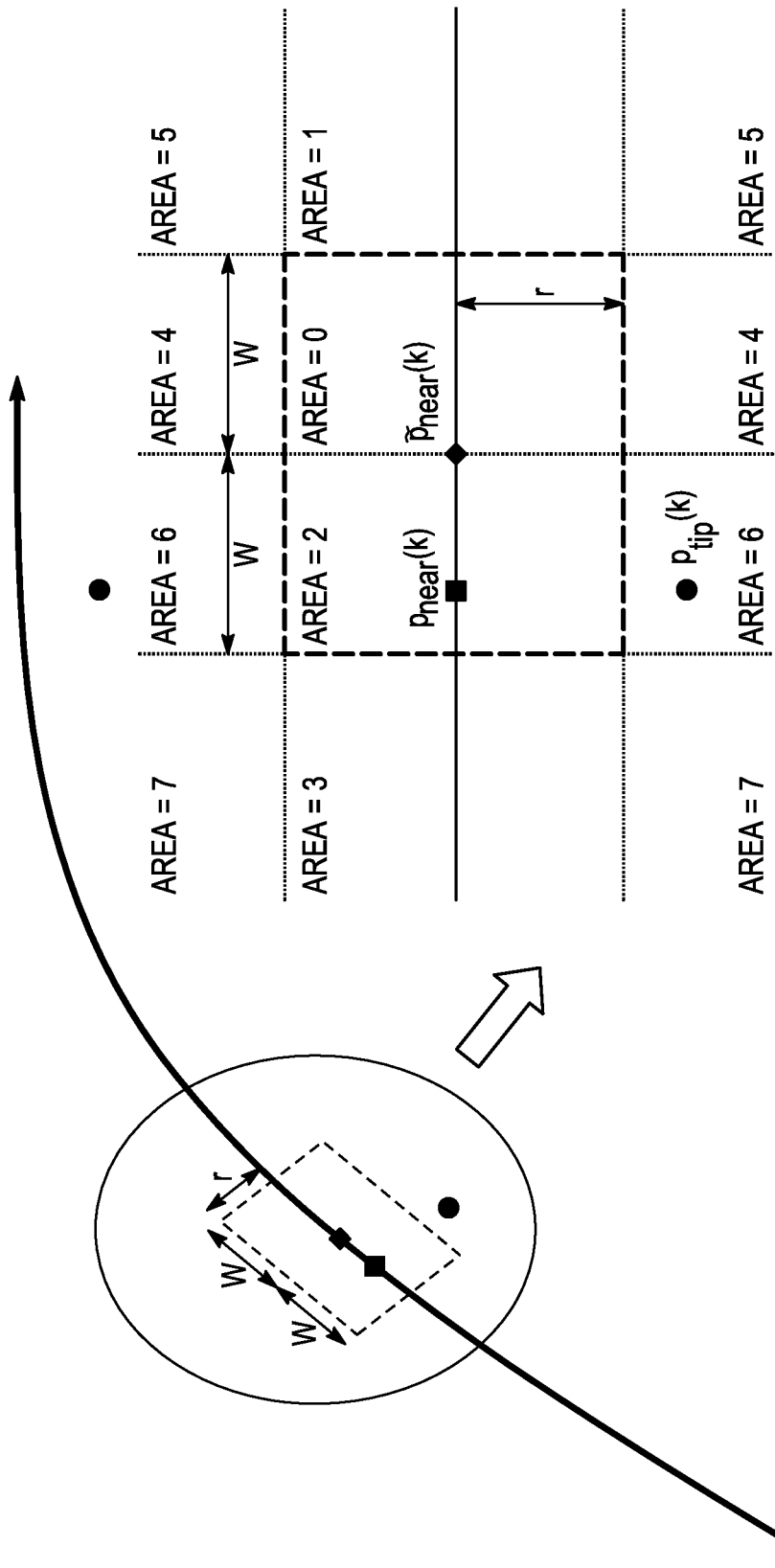
FIG. 10 shows a bounding box area for the attractive force generator's reference.

Given $\tilde{p}_{near}(k)$ with a tube radius (r) and a pre-defined width (W), a virtual rectangle whose center is $\tilde{p}_{near}(k)$ is defined as shown in FIG. 10. The inside and outside regions of the virtual rectangle are partitioned into eight areas. The area index (area=$\{0, 1, \ldots, 7\}$) is updated using the following steps.

Step 1. area(k)=0 //initialize
Step 2. if ($d_{dev}(k) \geq r$), then area (k)+=4
Step 3. if ($\langle v_{near}(k), v_{ref}(k) \rangle \leq 0$), then area(k)+=2, where $\langle .,. \rangle$ represents the inner product operator
Step 4. if ($w(k) \geq W$), then area(k)+=1

The following two cases unidirectional and bidirectional are considered to update $\tilde{p}_{near}$.

Case 1. Given a desired path, the force guidance system only allows moving toward the goal position ($p_m$). To generate this feedback force, $\tilde{p}_{near}$ is updated as follows:

$$\tilde{p}_{near}(k+1) = \begin{cases} p_{near}(k), & \text{if area}(k) \in \{0, 1, 4\} \\ \tilde{p}_{near}(k), & \text{otherwise} \end{cases}.$$

For instance, if a tool tip is inside of the virtual tube but it moves to reverse direction (e.g., $p_{tip}$ is in area 2), $\tilde{p}_{near}$ will keep the previous value to provide attractive force that guides a proper movement direction. If a tool tip moves in the forward direction but $w \leq W$ and $d_{dev}(k) \geq r$ (i.e., $p_{tip}$ is in area 4), $\tilde{p}_{near}$ will be updated to provide force feedback to minimize the deviation. When a tool tip is in area 5, $\tilde{p}_{near}$ will keep the previous value to indicate that the movement is wrong even if the direction is correct. The expected control behavior is as follows:

$$\text{ctrl\_action} = \begin{cases} \text{Free}, & \text{if area}(k) \in \{0, 1\} \\ \text{Guide}, & \text{otherwise} \end{cases}.$$

Case 2. Given a desired path, a tool tip can move freely inside a virtual tube. If the tool tip is moving outside of the virtual tube, the controller will generate attractive force. $\tilde{p}_{near}$ is updated as follows:

$$\tilde{p}_{near}(k+1) = \begin{cases} \tilde{p}_{near}(k), & \text{if area}(k) \in \{5, 7\} \\ p_{near}(k), & \text{otherwise} \end{cases}.$$

Unlike the unidirectional case, the modified nearest point will be updated in most of the areas. However, if the tool tip keeps deviating from the path and $p_{near}$ is not in a virtual rectangle (i.e., area 5 and 7), $\tilde{p}_{near}$ will keep the previous value to inform about an inappropriate movement. The expected control action is as follows:

$$\text{ctrl\_action} = \begin{cases} \text{Free}, & \text{if area}(k) \in \{0, 1, 2, 3\} \\ \text{Guide}, & \text{otherwise} \end{cases}.$$

Using $\tilde{p}_{near}$, the reference position $p_{attr}$ for a virtual tube is defined as follows:

$$p_{attr}(k) = \begin{cases} \tilde{p}_{near}(k) + r \cdot v_{dev}(k)/d_{dev}(k), \text{ for Guide} \\ p_{tip}(k), \text{ for Free} \end{cases}.$$

2 Switching Controller

Figure 11:
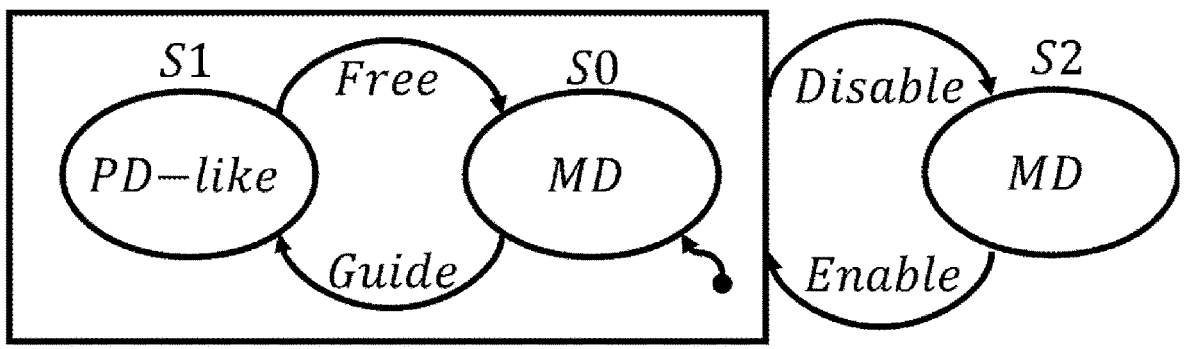
FIG. 11 shows an example of a switching controller for an attractive force.

A switching controller presented in FIG. 11 is implemented using PD-like and MD-type controllers. There are three states and each state has its own controller. A state transition is triggered based on control actions. Two more actions, Disable and Enable which are external control signals, are used to manage state transitions with Free and Guide actions. For instance, if a tool tip was in area 5 at k−1 and then the tip enters area 1 at k, the state transition (S1→S0) will have occurred to provide more control authority to a trainee. Thus, control output will be decreased due to the MD-type controller. Three independent switching controllers are implemented to control yaw, insertion, and pitch axis, respectively. Each switching controller has different parameters but the structure is the same.

Figure 12:
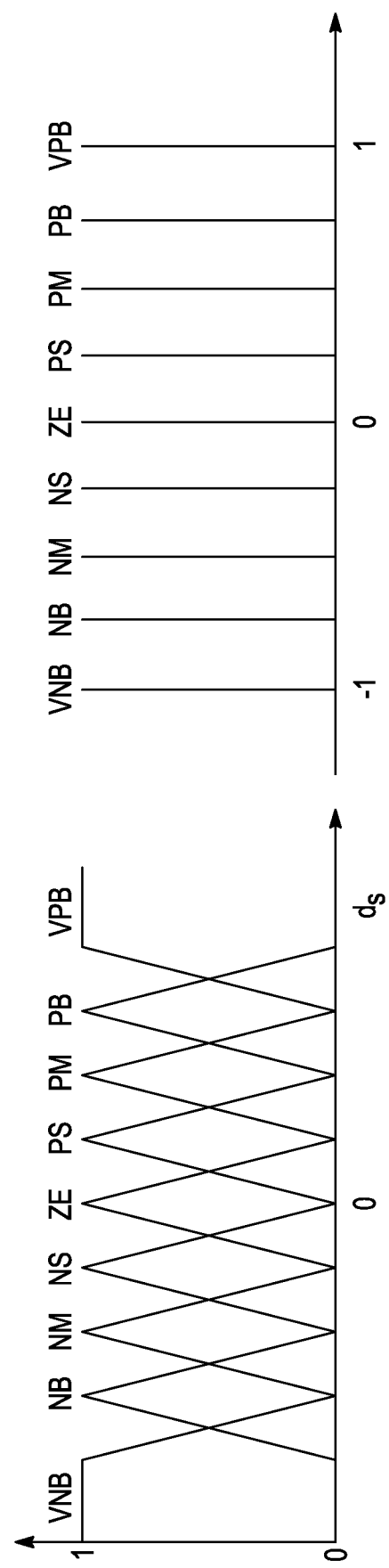
FIG. 12(A) shows rules tables for Sd-FSMC.
FIG. 12(B) shows fuzzy input membership functions and FIG. 12(C) shows fuzzy output membership functions.

The reference inputs $q_{attr}$ for PD-like controllers are obtained from $p_{attr}$. The error e is defined as follows:

$$e(k) = q_{attr}(k) - q_{tip}(k),$$

where the encoder counter values $q_{tip}$ are obtained from $p_{tip}$ and $e = (e^{yaw}, e^{ins}, e^{pit}, e^{rol}) \in \mathbb{N}^4$ where $e^{rol}$ is not used because there is no motor for the roll axis. To construct Sd-FSMC, nine fuzzy rules are used. The rule tables are depicted in FIG. 12(A). Input fuzzy sets and output fuzzy sets are also presented in FIG. 12(B) and FIG. 12(C), respectively.

B) Controllers for Assistive Force

Figure 13:
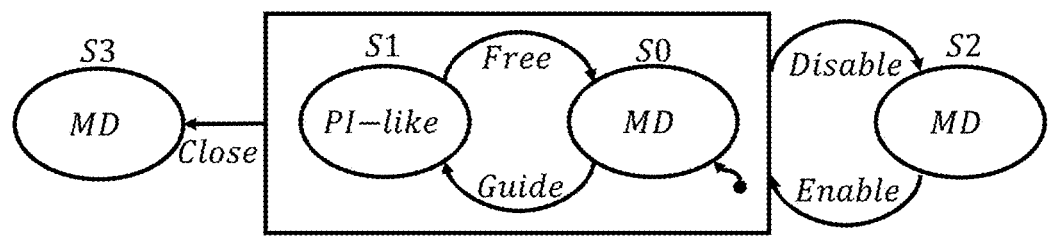
FIG. 13 shows another example of a switching controller for an attractive force.

The objective of these controllers is to provide force feedback for a trainee to follow a desired path. Position controllers are also implemented using a switching controller presented in FIG. 13. For this assistive force generation, PI-like and MD-type controllers are used with a virtual tube geometry. Given a desired path with a radius r, the virtual tube is created. The expected control action is as follows:

$$\text{ctrl\_action} = \begin{cases} \text{Close}, & \|p_{tip} - p_m\| < \delta \\ \text{Free}, & d_{dev} \geq r \wedge \|p_{tip} - p_m\| \geq \delta \\ \text{Guide}, & d_{dev} < r \wedge \|p_{tip} - p_m\| \geq \delta \end{cases},$$

where Free represents the fact that the controller reduces guidance force to prevent wrong operations and Guide indicates that a controller assists a trainee to follow the path. Also, Close action is generated if the remaining distance from $p_{tip}$ to $p_m$ on the path is less than a threshold distance $\delta$.

The reference position $p_{ass}$ for PI-like controllers is updated using the following equation:

$$p_{ass}(k+1) = p_{near}(k) + v \cdot v_{ref}(k)/\|v_{ref}(k)\|,$$

where $p_{ass}(0) = p_1$ and v is a constant reference speed. The error e is defined as follows:

$$e(k) = q_{ass}(k) - q_{near}(k),$$

where $q_{ass}$ and $q_{near}$ are the corresponding encoder counter values for $p_{ass}$ and $p_{near}$, respectively. As in the attractive force generator, nine fuzzy rules are used with triangular membership functions to characterize the input $d_s$ and singleton membership functions to describe the output ΔU.

Stability Analysis

The switching controllers are designed to generate guidance force under a human-in-the-loop configuration in discrete time domain.

A discrete Lyapunov function is defined as follows: $V(k) = d_s^2(k)/2$. Consider the change of V: $\Delta V(k) = V(k) - V(k-1) = d_s(k-1)\Delta d_s(k) + (\Delta d_s(k))^2/2$. If the control satisfies $d_s(k-1)\Delta d_s(k) \leq -(\Delta d_s(k))^2/2$ for $\forall k$, then a system is stable in the sense of Lyapunov. Because of nonlinearity and nondeterministic switching behavior, it is challenging to use conventional stability analysis. Therefore, we investigate trajectories of the system states to discuss the system stability based on multiple Lyapunov stability.

PD-like: Consider the trajectory of the SFM. There are 6 areas to represent heuristic rules as shown in FIG. 8. For each area $\mathcal{A}_i$ where $1 \leq i \leq 6$, there exist two sub-areas ($\mathcal{A}_i = \mathcal{A}_i^{unstable} \cup \mathcal{A}_i^{stable}$), $\mathcal{A}_i^{unstable}$ and $\mathcal{A}_i^{stable}$ represent an area that makes $\Delta V > 0$ and $\Delta V \leq 0$, respectively. We show that the PD-like controller can make a system stable for $\forall k \geq K$ if the trajectory of the SFM traverses only stable areas and $|d_s(k)| \leq \delta$ as $k \to \infty$ where $\delta$ is a small positive number for $\forall k \geq K$. To describe the characteristics of the controller, consider four cases with a trajectory analysis.

- $d_s(k-1) > 0$ and $\Delta d_s(k) > 0$: It indicates that $d_s(k) > d_s(k-1) > 0$, $u(k-1) > 0$, and $\Delta V > 0$. The SFM should adjust $G_u$ to make $\Delta V \leq 0$ using the corresponding heuristic rule. There are two sub-cases of $u_{avg}$. If $u_{avg} > 0$, then the trajectory is in $\mathcal{A}_1^{unstable}$. If $u_{avg} < 0$, then the trajectory is in $\mathcal{A}_3^{unstable}$ or $\mathcal{A}_2^{unstable}$. To make the system stable, the trajectory should exit the unstable region within a finite time by adjusting $G_u$.

- $d_s(k-1) > 0$ and $\Delta d_s(k) < 0$: It indicates that there exist areas with $\Delta V \leq 0$. If $u_{avg} > 0$, then the trajectory is in $\mathcal{A}_5$ or $\mathcal{A}_6$. If the trajectory traverses in $\mathcal{A}_5^{stable}$ or $\mathcal{A}_6^{stable}$, then the controller can make the system stable. If $u_{avg} < 0$, then the trajectory is in $\mathcal{A}_4$. If the trajectory traverses in $\mathcal{A}_4^{stable}$, then the controller can make the system stable as well.

- $d_s(k-1) < 0$ and $\Delta d_s(k) < 0$: It is similar to the first case.

- $d_s(k-1) < 0$ and $\Delta d_s(k) > 0$: It is similar to the second case.

There are two switching modes—additive increase ($sm_{inc}$) and multiplicative decrease ($sm_{dec}$) in the SFM. For $\forall k < K$, there is a finite number of switching and there exist states of the SFM such that $\Delta V_{sm_x} > 0$. However, if $V_{sm_x}(k) \leq V_{sm_x}(K)$ and the trajectory always traverses any $\mathcal{A}_i^{stable}$ (i.e. $\Delta V_{sm_x} \leq 0$) for $\forall k \geq K$, then the controller can make the system stable by satisfying $|d_s(k)| \leq \delta$ as $k \to \infty$ after time K. Depending on the tuning parameters and the behavior of SFM, there exists a chattering effect.

In H. Lee and V. I. Utkin, "Chattering suppression methods in sliding mode control systems," *Annu. Rev. Control*, vol. 31, no. 2, pp. 179-188, 2007, several chattering suppression methods such as observer-based, state-dependent gain, and hysteresis loop were discussed. The PD-like controller described herein is a state-dependent gain method which adjusts the switching gain to reduce chattering. To illustrate the chattering suppression, consider the following system (where the sampling interval is 0.05) with the three control laws as an example:

$$x(k+1) = \begin{bmatrix} 0.9988 & 0.04756 \\ -0.04756 & 0.9037 \end{bmatrix} x(k) + \begin{bmatrix} 0.001209 \\ 0.04756 \end{bmatrix} u(k),$$

Figure 14:
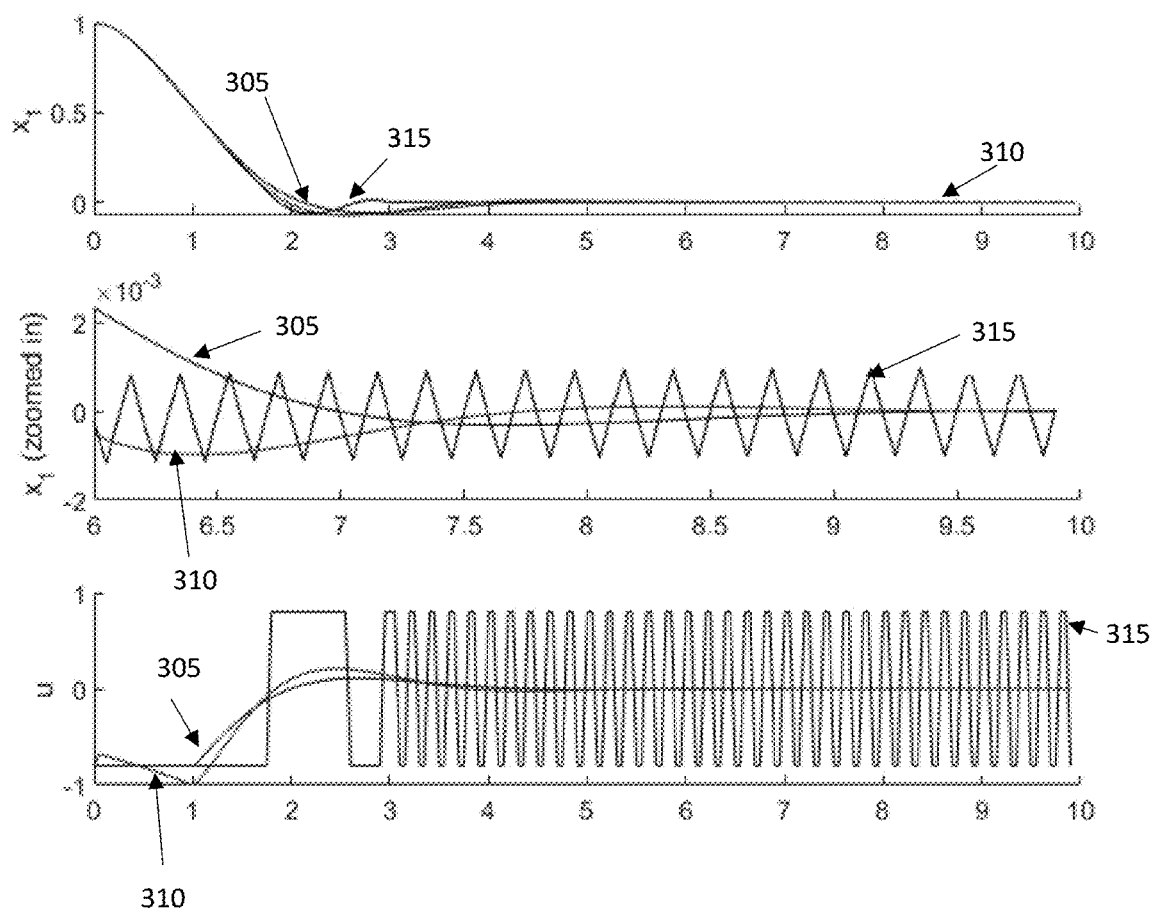
FIG. 14 shows simulation results illustrating that chattering is reduced by using $u_2$ (curve 305) and $u_3$ (curve 310) compared to $u_1$ (curve 315) with $G_0=0.8$.
Figure 15:
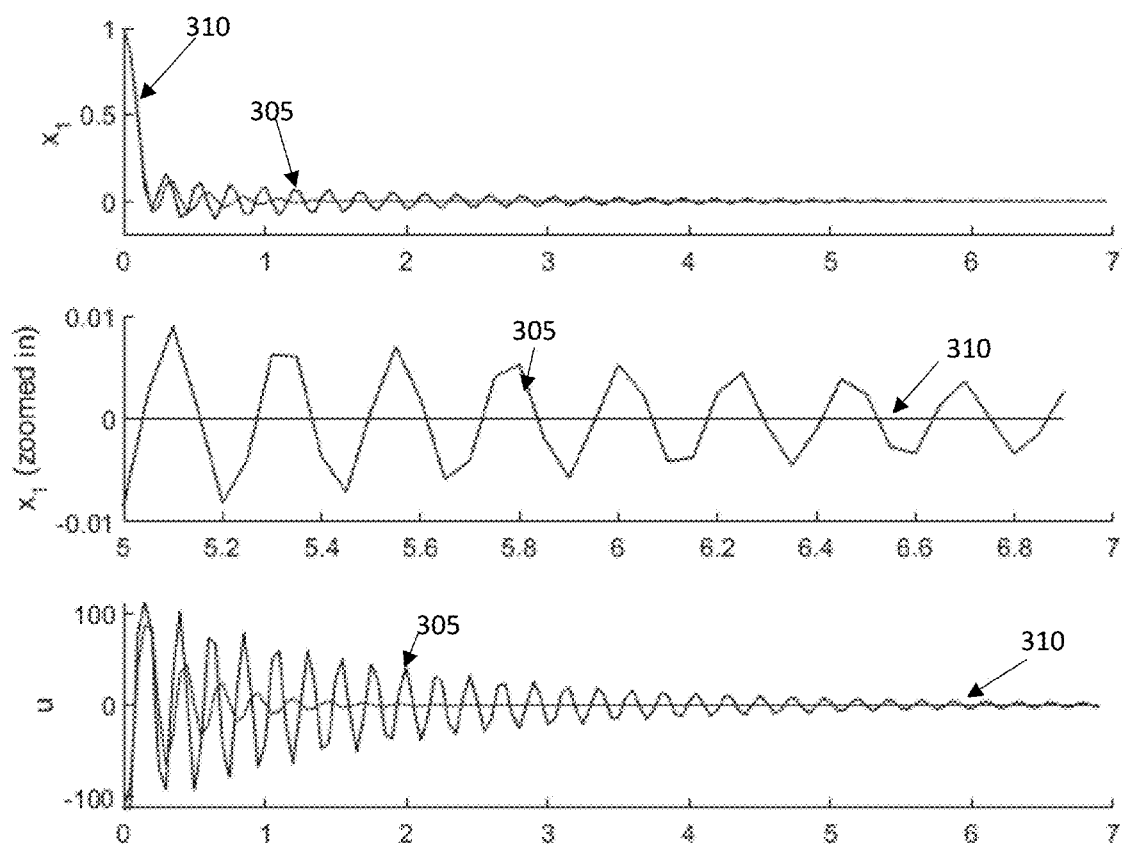
FIG. 15 shows simulation results illustrating that chattering is reduced using $u_3$ (curve 310) compared to $u_2$ (curve 305) when $G_0=112$.

$u_1=G_0 \cdot \text{sign}(d_s)$, $u_2=G_0 \cdot \text{sat}(d_s/d_{sMax})$, and $u_3=G_u \cdot \text{sat}(d_s/d_{sMax})$. Where $G_0$ is a constant switching gain and sat(•) is a saturation function bounded by $d_{sMax}$. $u_1$ is a standard sliding mode control, $u_2$ is a Sd-FSMC, and $u_3$ is our PD-like control. FIG. 14 shows the simulation results when $x(0)=[1\ 0]^T$, $G_0=0.8$, $\lambda=0.5$, $d_{sMax}=0.2$, $\lambda^G=\lambda/G_0$, $\alpha^G=0.05\ G_0$, and $\beta^G=0.3$. Unlike applying $u_1$, both $u_2$ and $u_3$ could minimize the chattering. To show the effectiveness of the gain adaptation, let us set $G_0=114$. The controller can adjust $G_u$ rapidly as well as reduce the chattering as shown in FIG. 15.

PI-like: The controller keeps a sign of u unless the direction is changed. Assume that there is no direction change. If the controller faces $d_s(k)d_s(k-1)<0$ at $k=K_{crossing}$ (i.e., switching mode from $sm_{inc}$ to $sm_{dec}$ like the SFM), then $|d_s(k+1)|\geq |d_s(k)|$ and $u\to 0$ for $\forall k \geq K_{crossing}$. It indicates that the system violates the multiple Lyapunov stability condition. However, the controller can meet the following statement:

$$V(k) \to V_{saturated} \wedge u(k) \to 0 \text{ as } k\to\infty (\forall k\geq K_{crossing})$$

During the surgical training, the direction stays the same for a certain amount of time. Therefore, the PI-like controller may cause an overshoot instead of chattering due to the multiplicative decrease with preserving the sign of u.

Switching controllers: Due to fact that a human is a dominant controller, the system stability highly depends on the human input. In state S1, the controller output u should make $\Delta V \leq 0$ for a human to make the system stable and ultimately switch to S0 or S3. In other states, u becomes zero as time progresses, therefore the human input determines stability. This human input may cause a state transition to S1 and make the system unstable as well.

A satisficing approach with set theory is used to discuss the system stability under this human-in-the-loop condition. The control input, u, is defined as follows: $u=u_{human}+u_{ctrl}$ where $u_{human}$ is the human input and $u_{ctrl}$ is the machine input. We define a satisficing control input set, U, to make the system stable as follows: $U=\{u:\Delta V\leq 0\}$. Likewise, the destabilizing set, $\tilde{U}$, is defined: $\tilde{U}=\{u:\Delta V>0\}$. U and $\tilde{U}$ are nonempty for all $x\neq x_d$. Also, $U\cap\tilde{U}=\emptyset$. Consider a special case that $u\approx u_{human}$ (i.e., $|u_{human}|>>|u_{ctrl}|$). In this case, the system stability purely depends on the human input. FIG. 16(A) depicts this case. A human operator can manipulate the surgical instrument perfectly by applying $u_{human}\in U_{human}$. The unstable situation is when he or she applies $u_{human}\in \tilde{U}_{human}$.

For the state S0, let us define a region, $R_{free}$, to indicate that a human operator has the full control authority: $R_{free}=\{x:V(x)\leq c_{free}\}$. In general, there exists an upper bound $c_{free}$ because $u_{human}$ and $u_{ctrl}$ are bounded. As time progresses, $u_{ctrl}\to 0$ and the system stability will depend on $u_{human}$.

Outside of $R_{free}$ represents the state S1. In this region, the controller will generate $u_{ctrl}$ to assist a human operator. The controller has two phases, adaption and post-adaptation, to drive x to $x_d$ within a finite time. During the adaptation phase, it cannot guarantee $\Delta V \leq 0$ but $V(k)\leq c_a$ where $c_a$ is an upper bound for $k\in[K_1, K_2]$. In the post-adaptation phase, there exists a stabilizing input set U as shown in FIG. 16(B). $u_{ctrl}$ can make the system stable by compensating the destabilizing $u_{human}$ (i.e., $U\cap\tilde{U}_{human}$; gray area in FIG. 16(B)). Also, $u_{ctrl}$ can make the system unstable due to using improper parameters even though applying stabilizing $u_{human}$ (i.e., $\tilde{U}\cap U_{human}$). There exists a case that $u_{ctrl}$ cannot compensate $\tilde{U}_{human}$ because the machine is an adjunctive controller.

Illustrative Results

A simple wire transfer task was designed to verify the adaptive force guidance system described herein. This task consists of four basic actions (as shown in FIG. 17), namely: a) move an instrument toward a ring, b) grasp the ring (r=10 mm), c) carry the ring to a goal position without touching the wire (60 mm (W)×42 mm (H)), and d) place the ring on a goal position. To determine a transition condition (e.g., from move to grasp), a reasoning procedure with a color object detection method was used. First, a single test user was asked to perform this task to evaluate the controllers under a certain condition. Second, we evaluated the effectiveness of the adaptive orce guidance with multiple testers.

A) Test Arrangement

Only single instrument for the right hand was used to perform the wire transfer task. DC motors with servo controllers (Maxon Motor, Switzerland) were used to support the force guidance system. Optical encoders with a data acquisition device (US Digital, USA) which enables to communicate between a standard PC and servo controllers were also used to trace the instrument's movement. To control the motors, a current control method was used by applying a set value (u). The set values are limited to [−2000, 2000], [−3000, 3000], [−3500, 3500] for yaw, insertion and pitch, respectively. Due to using a PC as a central processing system, the control frequency was relatively slow (i.e., 20 Hz under Windows OS).

For each action, the following geometries were used to generate the attractive force.

Move: a tube (r=2 mm); Grasp: a sphere (r=10 mm)
Carry: a tube (r=1 mm); Place: a sphere (r=20 mm)

The assistive force was generated only for the move action using a tube (r=5 mm) geometry.

The following key parameters were used for PD-like Sd-FSMCs.

Range of $G_u$: [100, 5000] for yaw, [100, 8000] for insertion, and [100, 8000] for pitch
Default $G_u$: 1000 for yaw and 1500 for insertion and pitch
$\lambda$ and $\lambda^G$: 0.5 and 1.0, respectively, for all axes
$\alpha^G$: 200 for yaw and pitch; 250 for insertion
$\beta^G$: 0.2 for yaw, 0.1 for insertion, and 0.05 for pitch
For PI-like Sd-FSMCs, the key parameters are as follows:
$\lambda$: 1.0 for all axes
$\kappa$: 75 for yaw, 100 for insertion, and 225 for pitch
$\gamma$: 0.8 for yaw, 0.85 for insertion, and 0.8 for pitch
where all the tuning parameters were determined based on the initial experimental results to adjust outputs of the controllers.

B) Evaluation of the Basic Operation

Figure 18A:
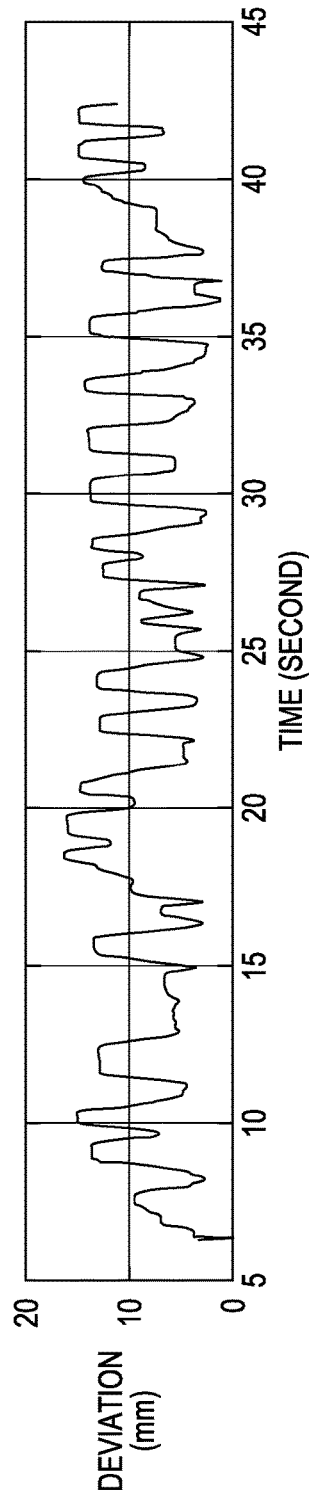
FIG. 18(A) shows the deviation for an attractive force that is generated for a sphere geometry.
Figure 18B:
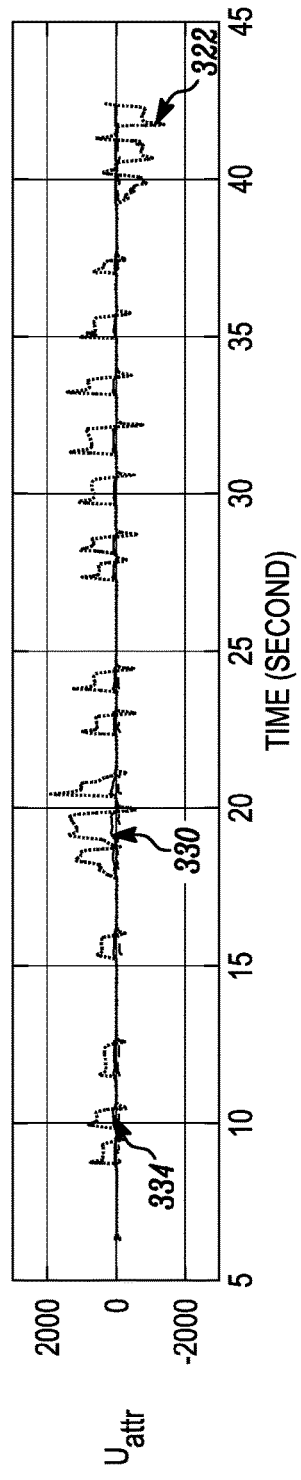
FIG. 18(B) shows the control outputs for an attractive force, where curves 330, 332 and 334 represent yaw, insertion and pitch, respectively.
Figure 18C:
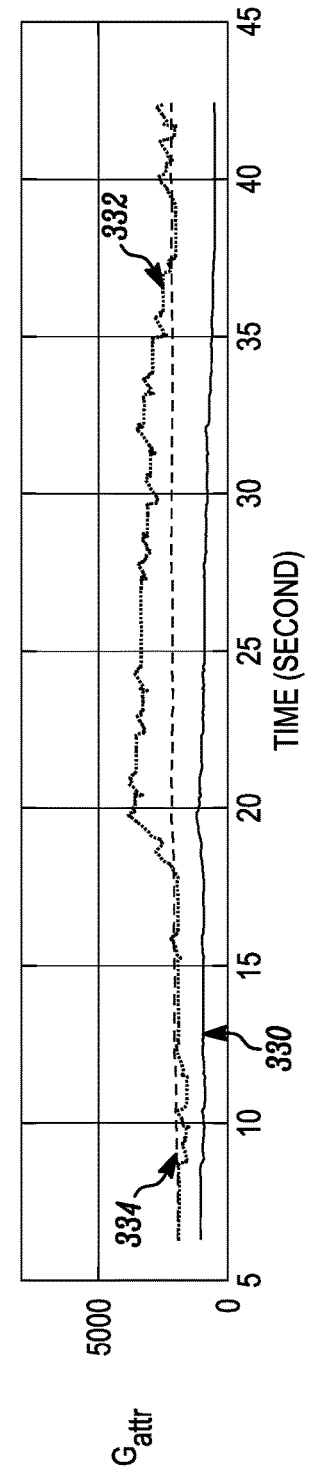
FIG. 18(C) shows the output scaling factors that are used.

To verify the basic operation of PD-like Sd-FSMCs, grasp and carry actions were used. Given a sphere geometry, the attractive force is generated whenever the tip of the instrument is located outside of the sphere. A single tester intentionally moves the instrument tip towards the outside of the sphere. Whenever the deviation is greater than r, the controllers generate attractive force to guide a trainee as shown in FIG. 18(B). The insertion axis (i.e., y-axis) motion was the dominant movement. Therefore, the corresponding control output ($u_{attr}^{ins}$) was applied to minimize the deviation by adjusting the output scaling factor ($G_{attr}^{ins}$) as shown in FIG.

18(C). Due to using the sphere surface as a switching surface, the tester could deviate more than expected (FIG. 18(A)).

Figure 19A:
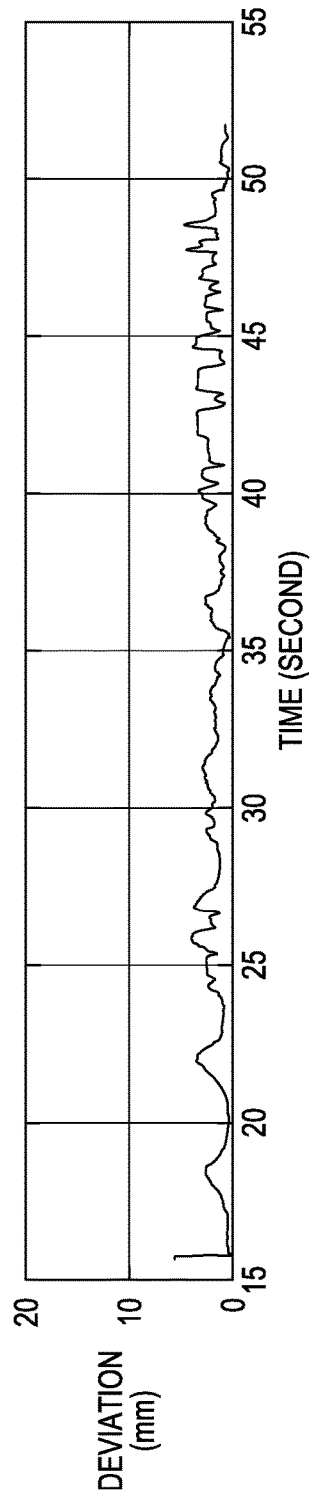
FIG. 19(A) shows the deviation from a reference path.
Figure 19B:
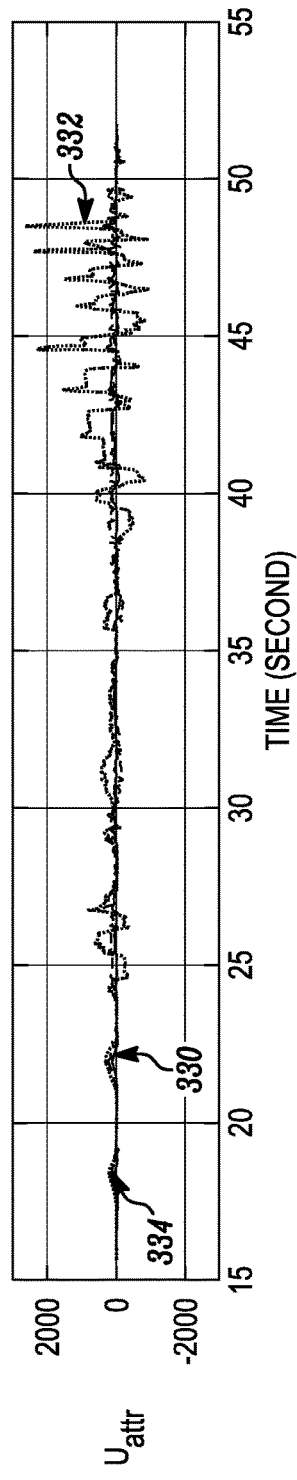
FIG. 19(B) shows the control outputs for an attractive force for a bidirectional guidance mode.
Figure 19C:
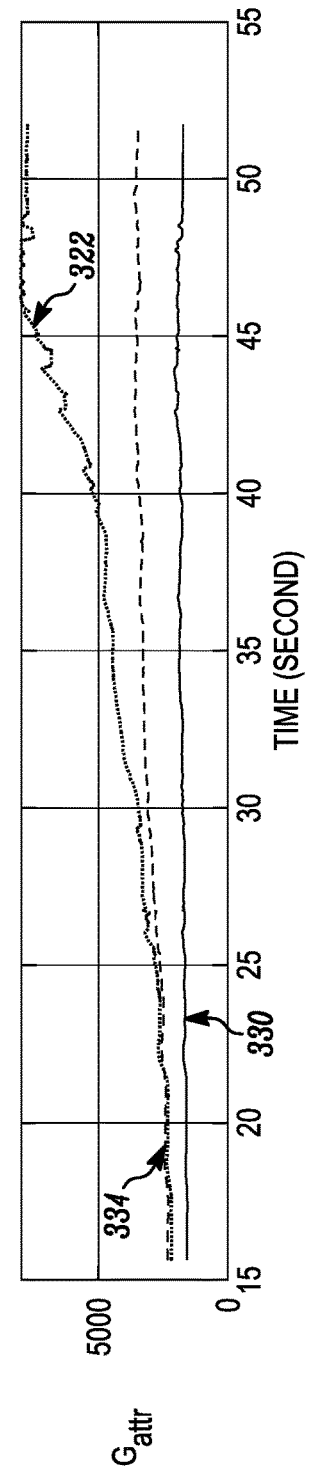
FIG. 19(C) shows the output scaling factors that are used.

To guide a trainee for the carry action, tube geometry was used. Given the tube, bidirectional or unidirectional motion was allowed by the attractive force. As in the sphere case, the single tester was asked to transfer the ring from T2 to T1. During the operation, the tester intentionally tried to move backward to verify the operation of the controller. The tester could make the reverse motion (i.e., move to +x axis) without any restrictions. FIG. 19(B) shows the control outputs. $u_{attr}^{ins}$ was the dominant control output to minimize the deviation (FIG. 19(A)) from the desired path. The output scaling factor ($G_{attr}^{ins}$) was adjusted to provide the proper feedback as shown in FIG. 19(C).

Figure 20A:
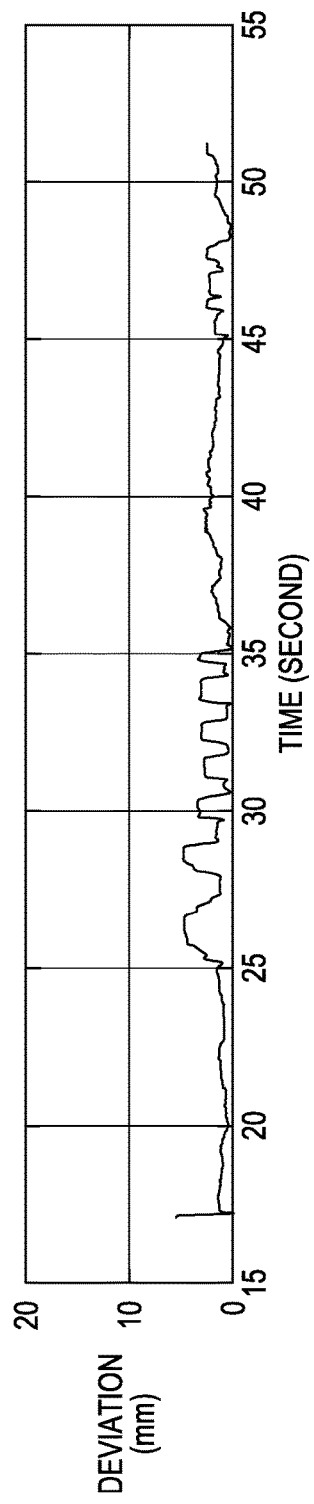
FIG. 20(A) shows the deviation from a reference path.
Figure 20B:
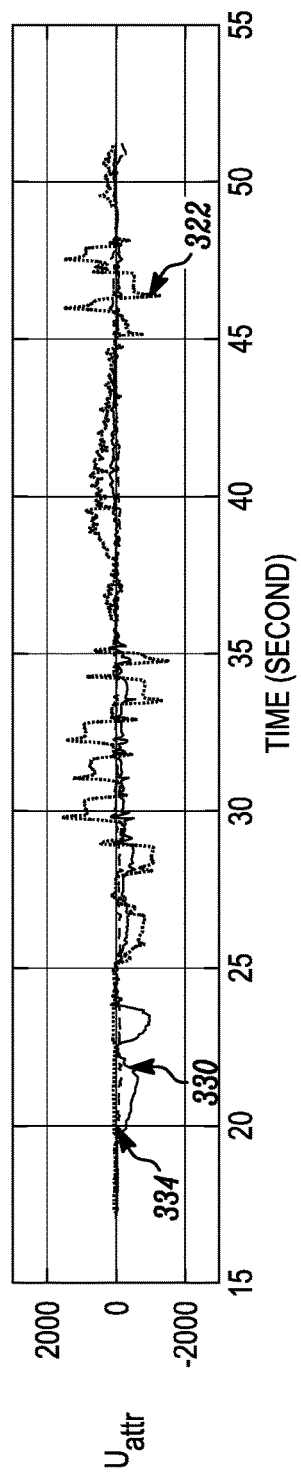
FIG. 20(B) shows the control outputs for an attractive force for a unidirectional guidance mode.
Figure 20C:
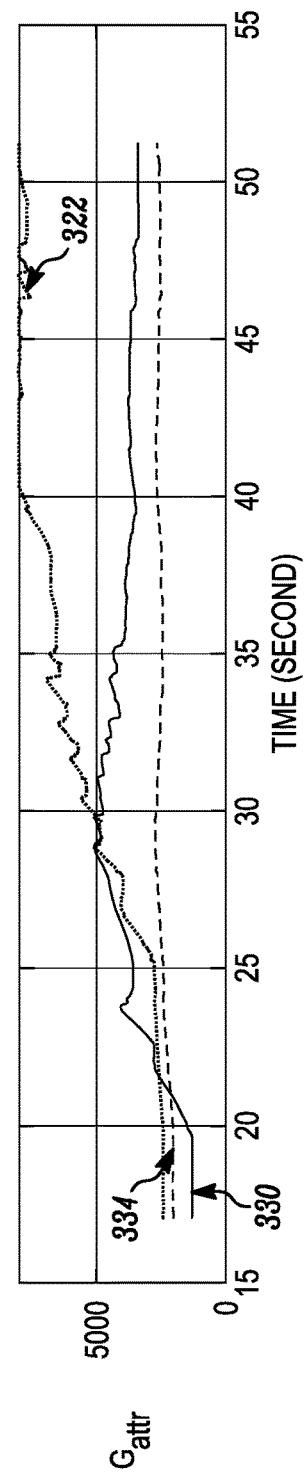
FIG. 20(C) shows the output scaling factors that are used.

As opposed to the bidirectional mode, the force guidance system restricts the backward motion to teach a trainee to move an instrument toward the goal position under the unidirectional mode. FIG. 20 illustrates this unidirectional mode operation. When the tester tried to move backward (between 20 and 25 seconds), the control output $u_{attr}^{yaw}$, was generated to restrict the motion. The output scaling factors also were adjusted to provide the proper force feedback.

The operation of the PI-like Sd-FSMC is presented in the following section.

C) Evaluation of the Effectiveness of the Force Guidance

Important objectives of the controllers described herein are as follows: O1) minimize a deviation from a reference by providing attractive force, O2) guide a trainee to traverse a desired trajectory by providing assistive force, O3) adjust amount of force for each individual trainee, and O4) allow much more control authority whenever a trainee performs well. To verify whether the controllers met the objectives, eight testers were asked to perform the wire transfer task four times. For each trial, the guidance system used one of the following aid methods: no guidance, visual guidance, force guidance type 1, and force guidance type 2. The order of the aid method was determined by a balanced Latin square design method.

In A. Wagner and J. W. Rozenblit, "Augmented Reality Visual Guidance for Spatial Perception in the Computer Assisted Surgical Trainer," in *Proceedings of the Symposium on Modeling and Simulation in Medicine. Society for Computer Simulation International*, 2017, pp. 855-866, several visual guidance cues were rendered (e.g., 2D circle, cube, and post) on a live camera image to assist a trainee in instrument navigation. For the visual guidance method, we rendered a recommended path, arrows, and posts as shown in FIG. 17. Table 1 shows the details of two force guidance methods for each action. If a tester dropped the ring or "broke" the wire, the test session would stop immediately.

TABLE 1

| Force guidance configuration | | |
|---|---|---|
| Actions | Force guidance type 1 | Force guidance type 2 |
| Move | Attractive + Assistive (unidirectional) | Attractive (unidirectional) |
| Grasp | Attractive | Attractive |
| Carry | Attractive (unidirectional) | Attractive (bidirectional) |
| Place | Attractive | Attractive |

TABLE 2

| | Incompletion cases | | |
|---|---|---|---|
| | Ring drop | | Wire drop |
| Aid methods | Grasp | Carry | Carry |
| No guidance | 1 | | 2 |
| Visual | 1 | 1 | 2 |
| Force type 1 | 2 | 1 | |
| Force type 2 | 1 | 1 | |

Two video instructions were played before performing the task to illustrate how to use the system and to explain the task. While executing, the guidance system collected data to evaluate the effectiveness of the system objectively by using captured instrument movements and control information. To evaluate the system subjectively, the guidance system asked the testers questions about the force guidance, specifically: 1) While performing this session, did you feel any kind of force feedback/guidance? 2) How about force feedback? Is it helpful? 3) How about visual feedback? Is it helpful?

Only three testers could complete the four trials without any drops. Table 2 shows the incompletion cases under a certain guidance condition. The main cause of the incompletion was the ring drop (about 25%). The present guidance system focused on assisting an instrument movement rather than maneuvering a grasper such as opening/closing (attractive force for grasp action just minimizes a deviation from the grasping point). Therefore, most testers had difficulty using the grasper. With force guidance, all testers could have avoided the wire drop.

Four evaluation metrics were used to assess the force guidance system. The metrics are as follows:
Completion time ratio=$(CT_{actual}-CT_{ref})/CT_{ref}$
Path length ratio=$(PL_{actual}-PL_{ref})/PL_{ref}$
Maximum deviation from a recommended path
Average deviation from a recommended path
where $CT_{actual}$ and $CT_{ref}$ represent the actual completion time and reference completion time. Similarly, actual path length and reference path length were used. If the ratio is close to zero, it indicates that the performance is good.

Figure 21:
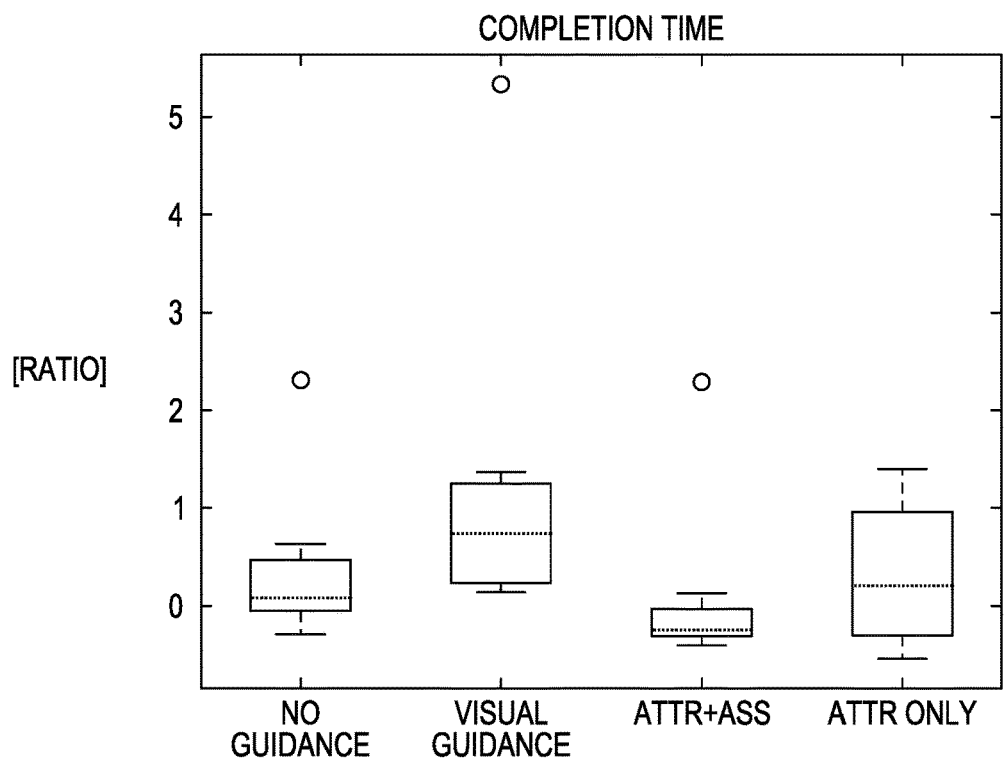
FIG. 21 illustrates box plots to present the effectiveness of four guidance methods for the move action.
Figure 21B:
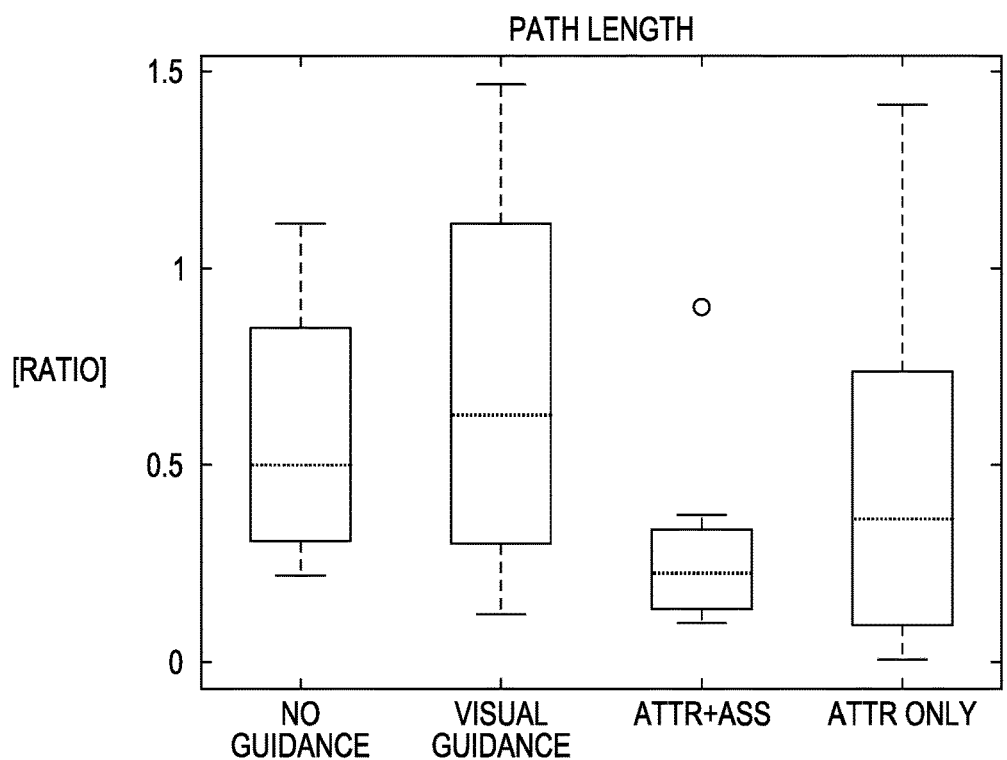
Figure 21C:
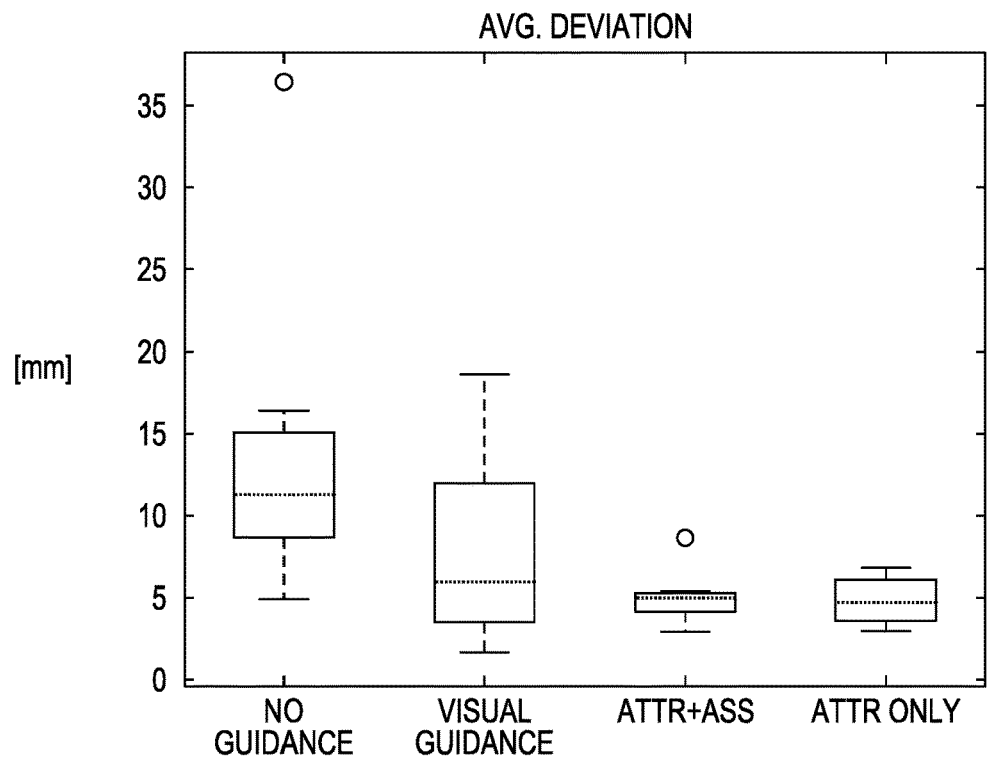
Figure 21D:
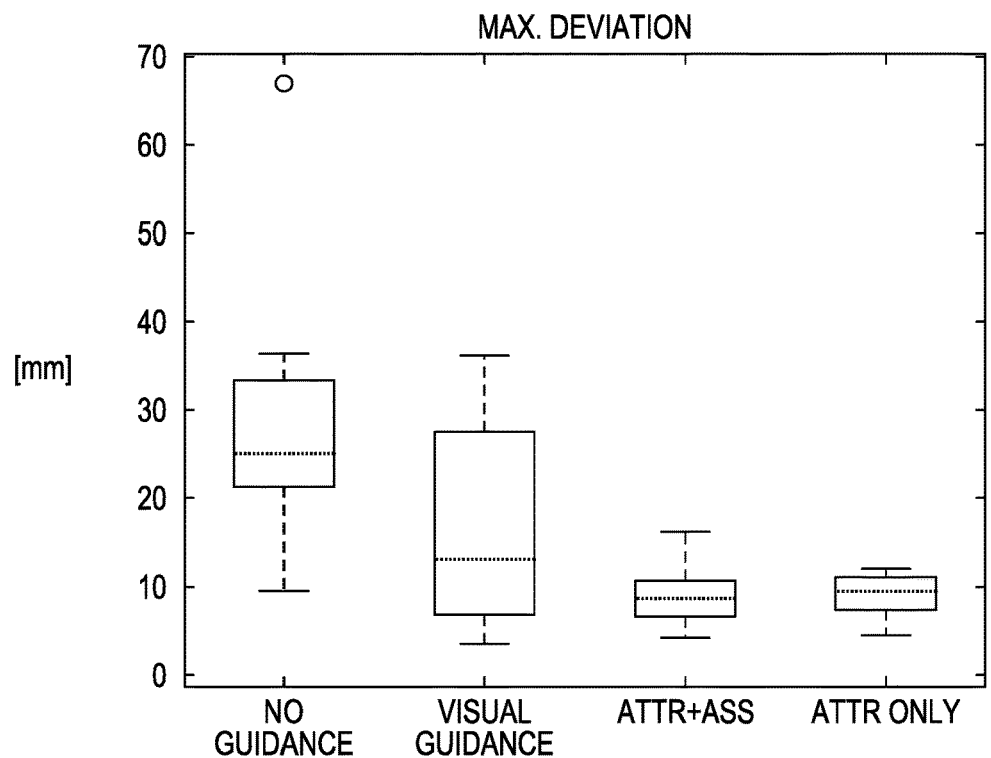
Figure 22A:
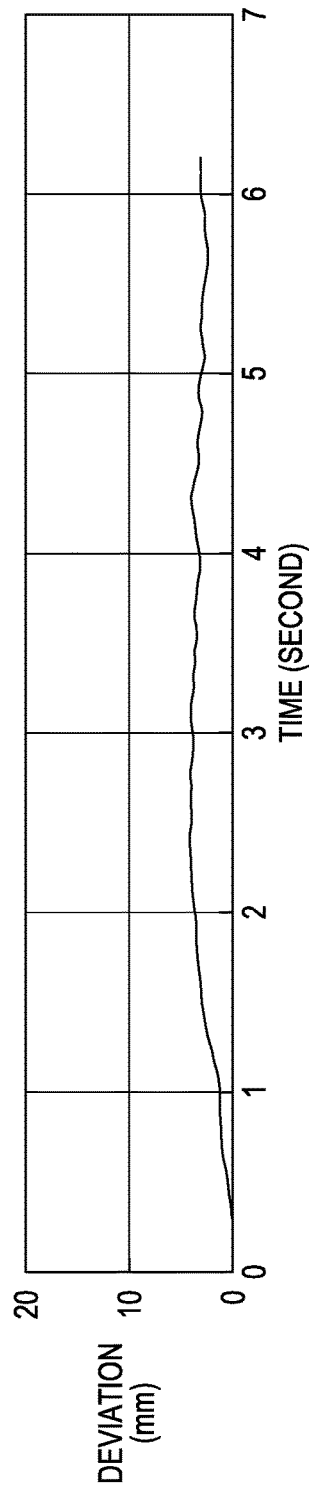
FIG. 22(A) shows the deviation from a reference path for a move action.
Figure 22B:
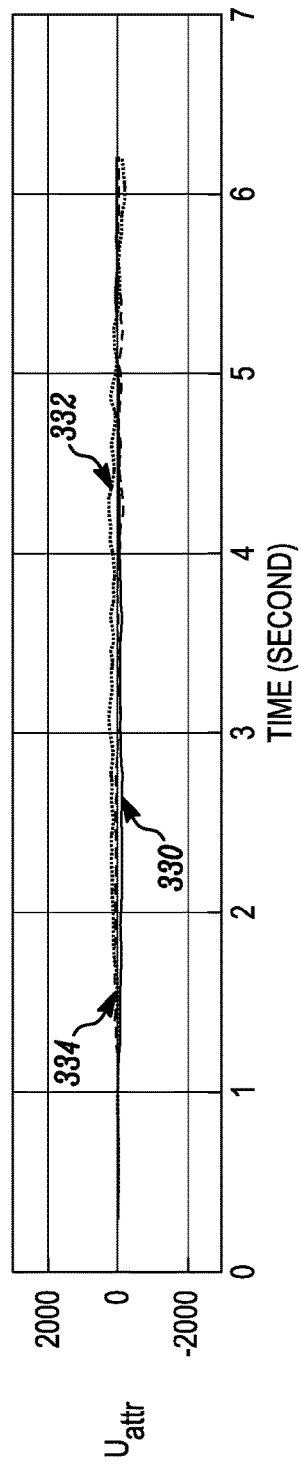
FIG. 22(B) shows the control outputs for a first example of an attractive force.
Figure 22C:
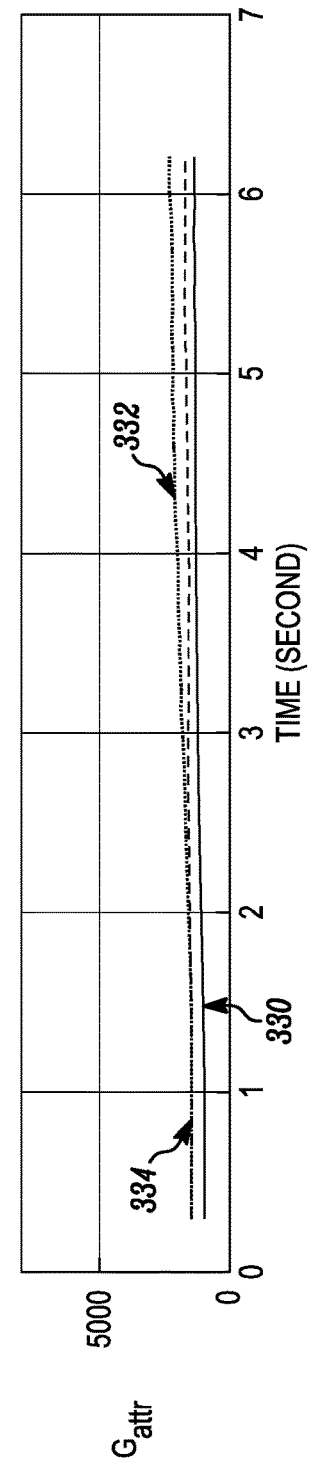
FIG. 22(C) shows the output scaling factors that are used.
Figure 22D:
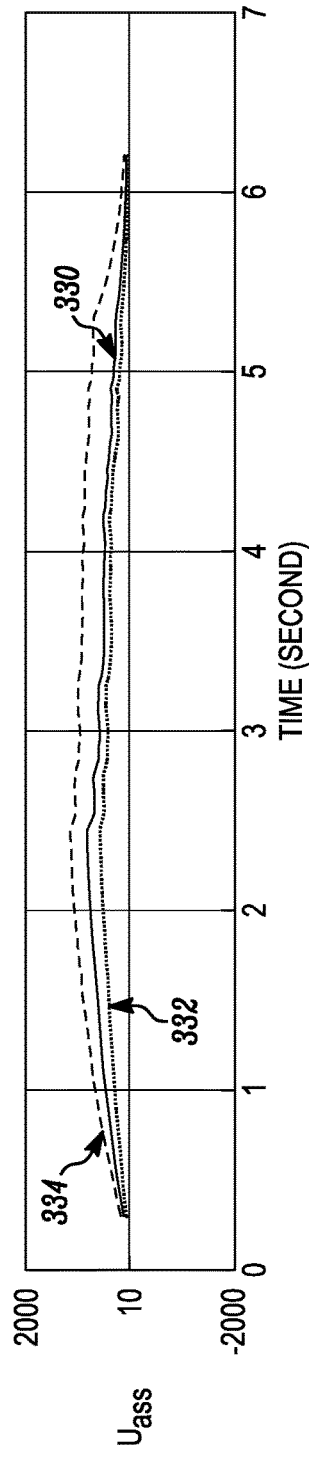
FIG. 22(D) shows the control outputs for an assistive force.
Figure 23A:
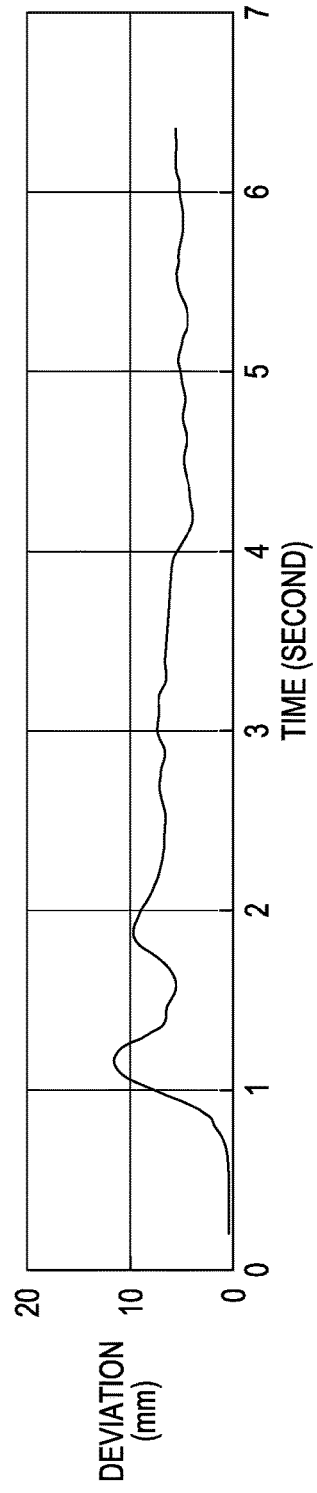
FIG. 23(A) shows the deviation from a reference path for a move action.
Figure 23B:
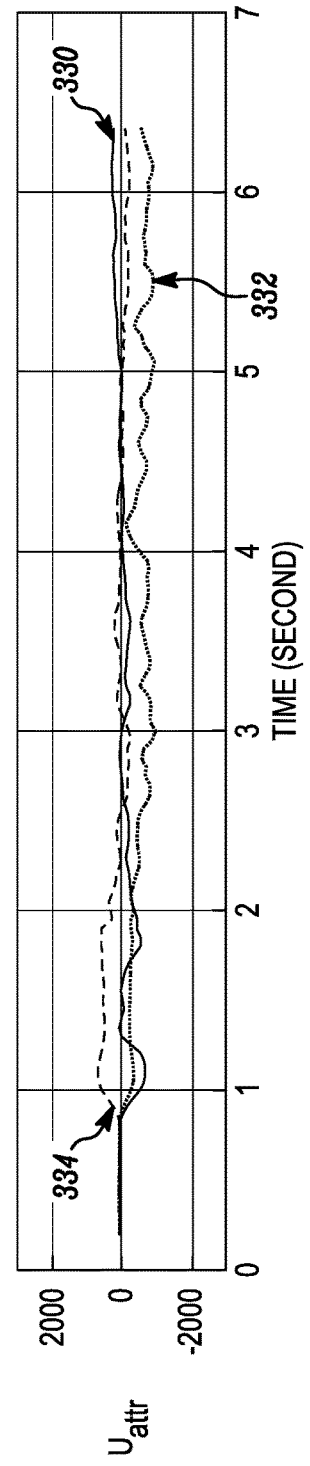
FIG. 23(B) shows the control outputs for a second example of an attractive force.
Figure 23C:
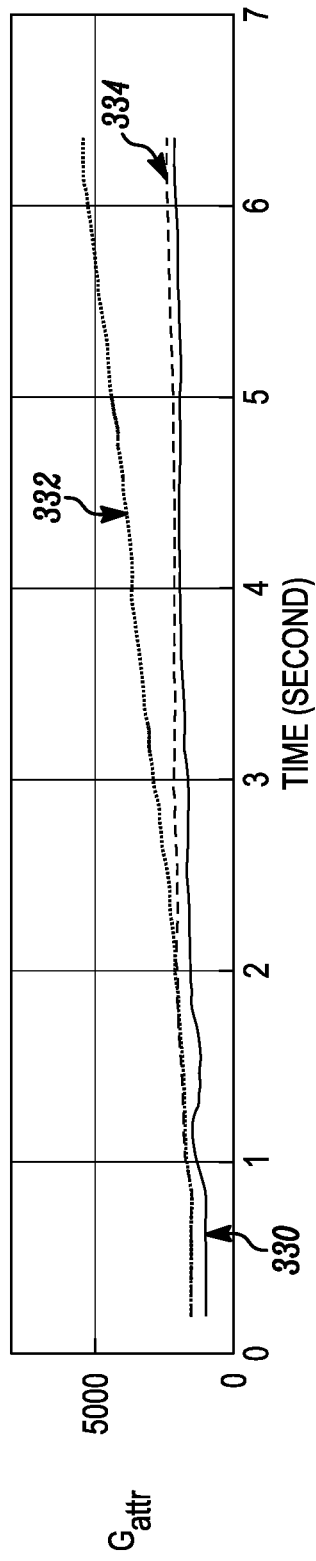
FIG. 23(C) shows the output scaling factors that are used.
Figure 23D:
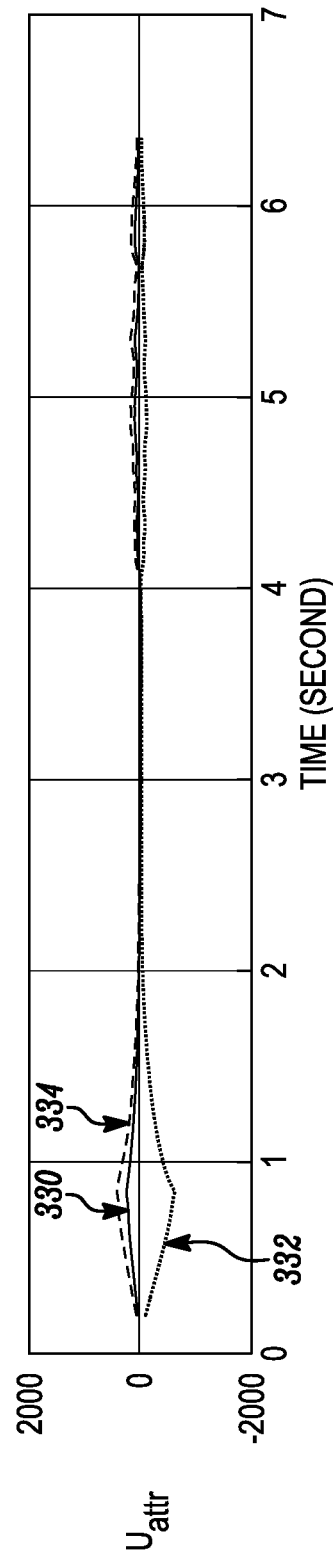
FIG. 23(D) shows the control outputs for an assistive force.

FIG. 21 illustrates box plots to present the effectiveness of four guidance methods for the move action. When the guidance system provided assistive and attractive force, most testers could complete the task quickly without large deviations. Also, the path length was managed effectively. Unlike the force guidance, the visual guidance did not restrict actual motions. Therefore, most testers could not mange path length and completion time well even though the visual navigation was enabled. In terms of deviations, both visual and force guidance methods could minimize the deviations from the ideal trajectory.

Figure 24A:
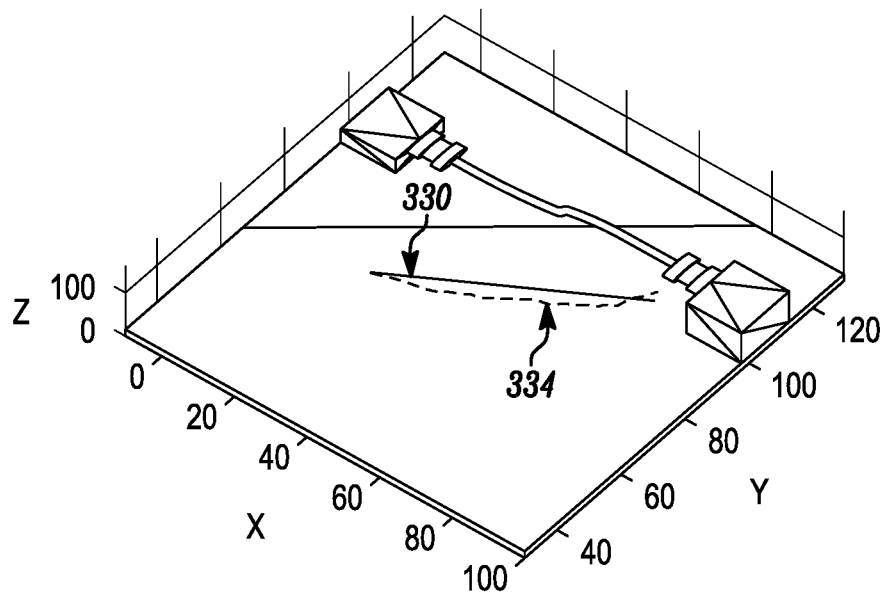
FIG. 24 shows the instrument tip trajectories (curve 334) and desired paths (curve 330) for, from top left to bottom right: the first example of force guidance for the move action, the second example of force guidance for the move action, the first example of force guidance for the carry action and the second example of force guidance for the carry action.
Figure 24B:
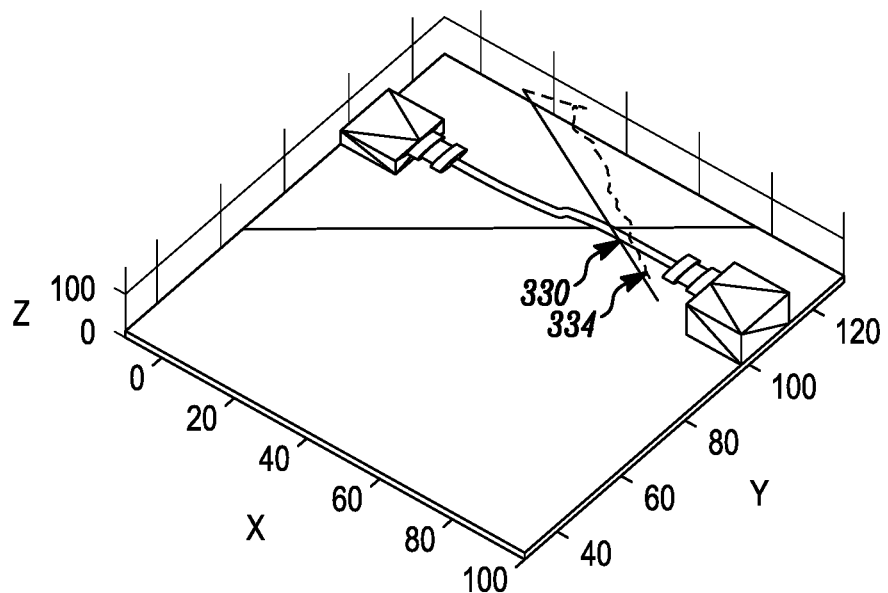

Two examples of force guidance type 1 are depicted in FIG. 22 and FIG. 23, respectively. If a trainee maintains the deviation well (i.e., the instrument tip is inside the virtual bounds), the assistive force would be applied to teach the trainee as shown in FIG. 22. Otherwise, the force guidance system applies attractive force mainly to minimize the deviation most of time as shown in FIG. 23. The trajectories are illustrated in FIGS. 24(A) and 24(B).

The effectiveness of the guidance methods for the carry action is presented in FIG. 25. There was no significant improvement in terms of completion time even though force guidance was applied. However, most testers could finish relatively quickly under the unidirectional guidance mode. The bidirectional mode had large time variations due to the system allowing backward motion. Under both force guidance schemes, there were huge improvements for path length and deviations. This indicates that the force guidance system described herein assists a trainee effectively (i.e., this guidance system teaches a trainee how to properly execute movement). Like the move action, most testers could maneuver the instrument without any restrictions under the visual guidance. The visual guidance could not improve any performance metrics unlike the progress observed with the move action.

Figure 26A:
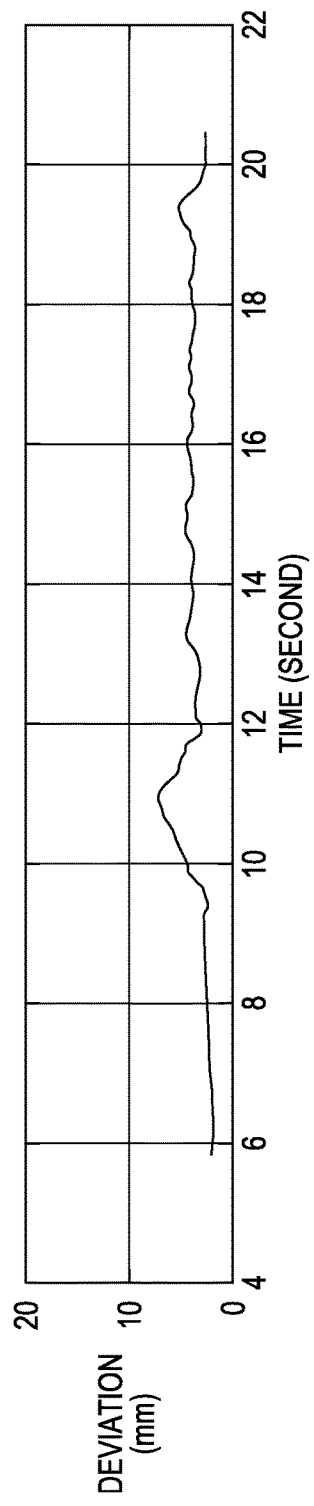
FIG. 26(A) shows the deviation from a reference path for a carry action.
Figure 26B:
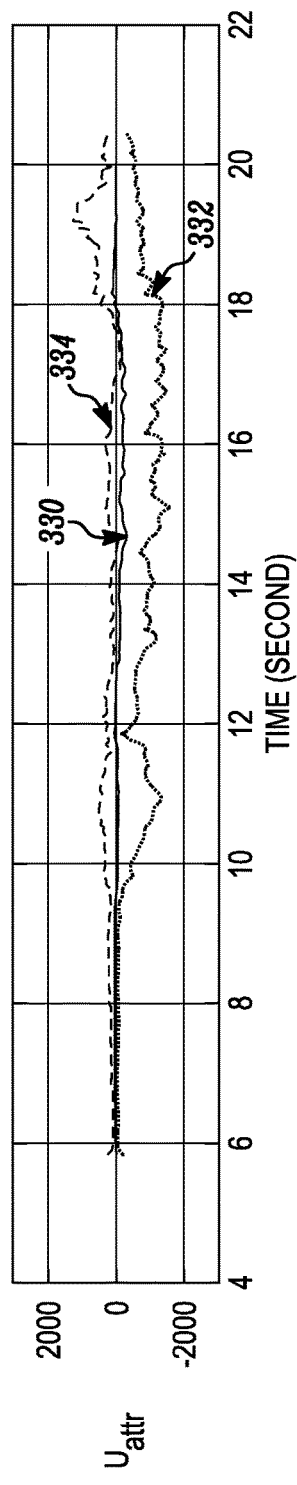
FIG. 26(B) shows the control outputs for a first example of an attractive force for the carry action.
Figure 26C:
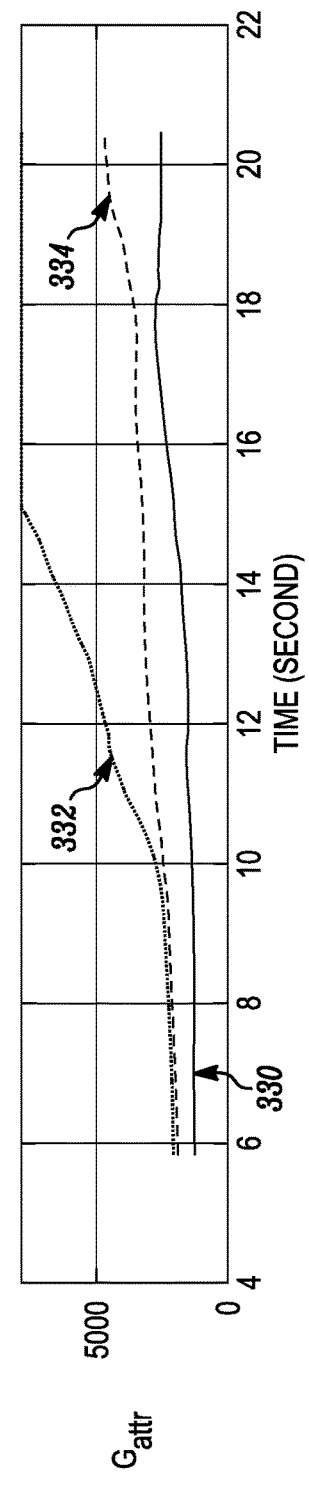
FIG. 26(C) shows the output scaling factors that are used.
Figure 27A:
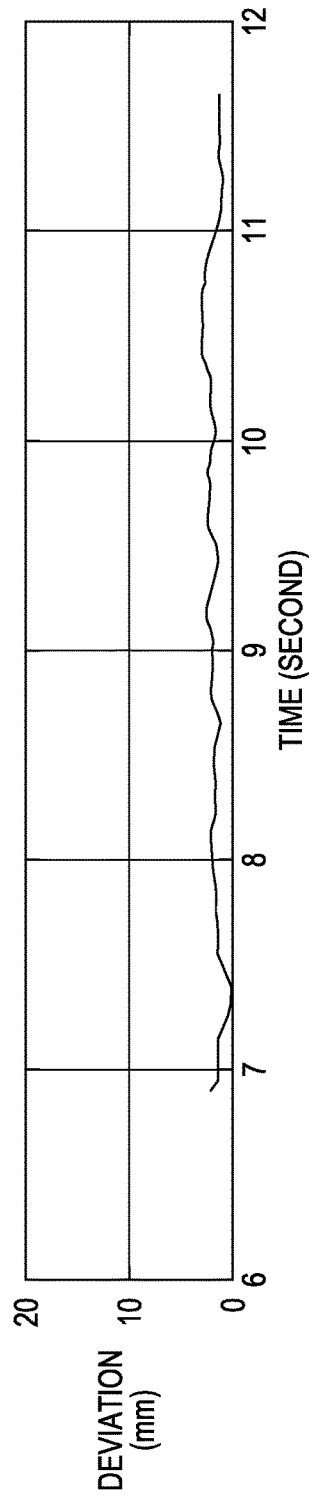
FIG. 27(A) shows the deviation from a reference path for a carry action.
Figure 27B:
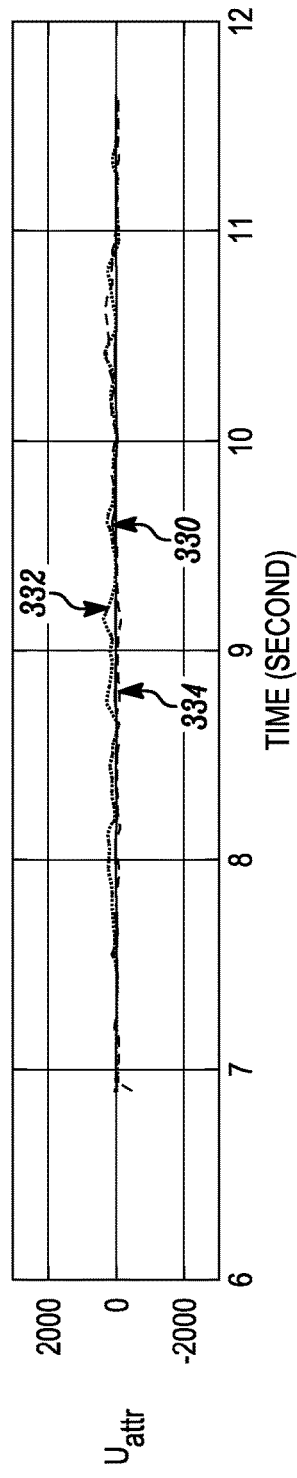
FIG. 27(B) shows the control outputs for a second example of an attractive force for the carry action.
Figure 27C:
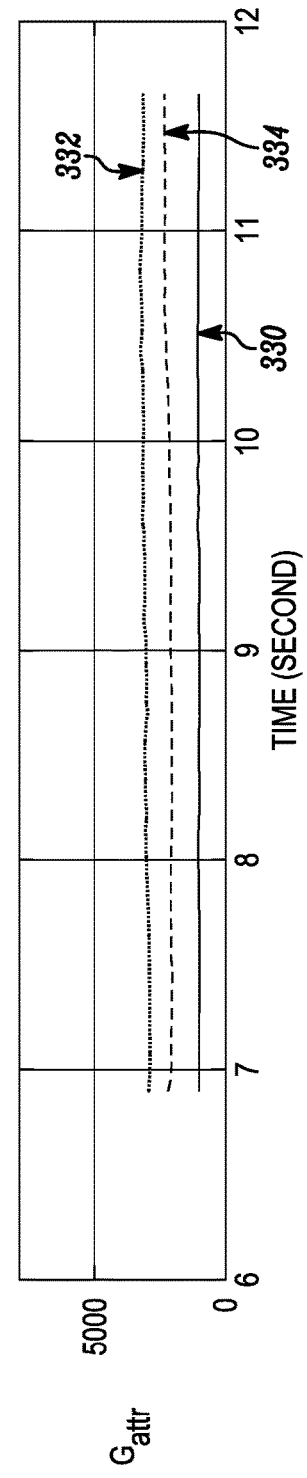
FIG. 27(C) shows the output scaling factors that are used.

FIG. 26 and FIG. 27 illustrate two examples of force guidance for the carry action. If a trainee had difficulty to maintain a proper distance from the wire while carrying the ring, the attractive force would be applied to guide a trainee to

TABLE 3

Subjective evaluation result about the force sensitivity

| | ← Weak force | | | Strong force → | |
|---|---|---|---|---|---|
| | 0 | 1 | 2 | 3 | 4 | 5 |
| Type 1 | 1 | | | 7 | | |
| Type 2 | 1 | | | 4 | 3 | |

TABLE 4

Subjective evaluation of guidance methods

Figure 24C:
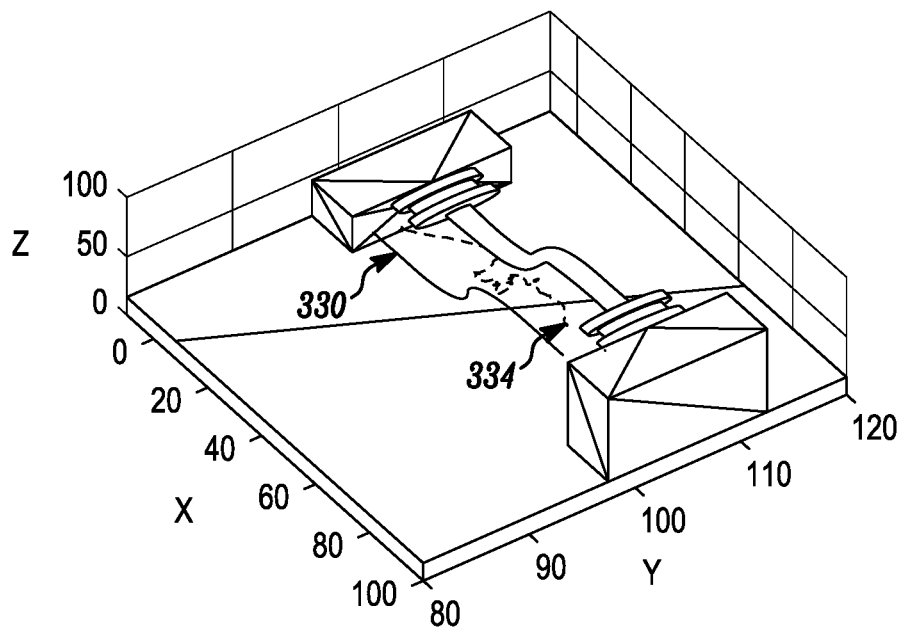
Figure 24D:
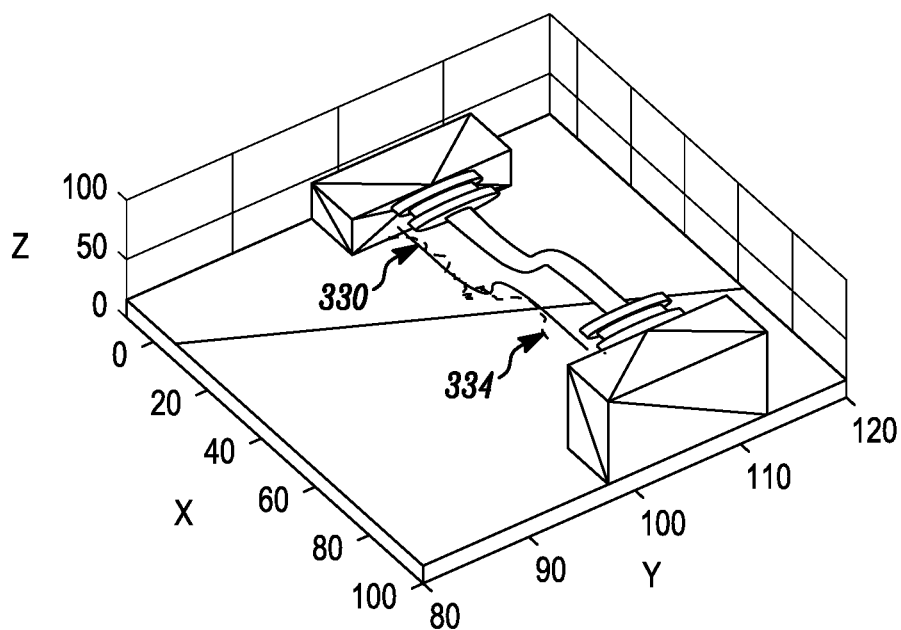
Figure 25A:
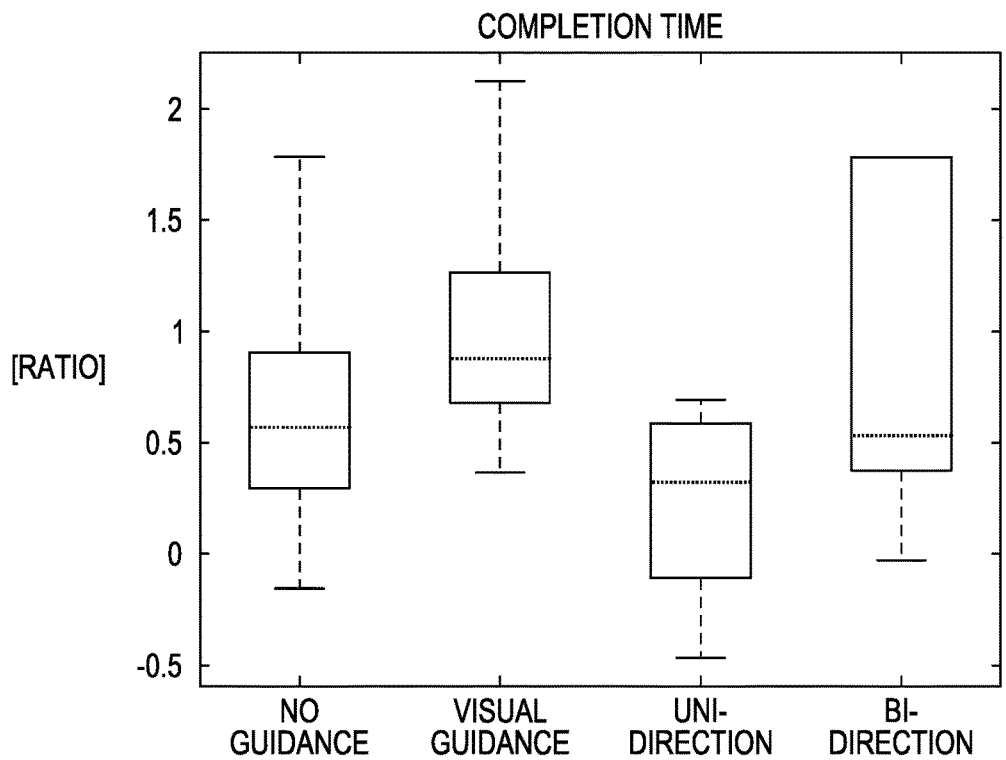
FIG. 25 shows the evaluation metrics for the carry action.
Figure 25B:
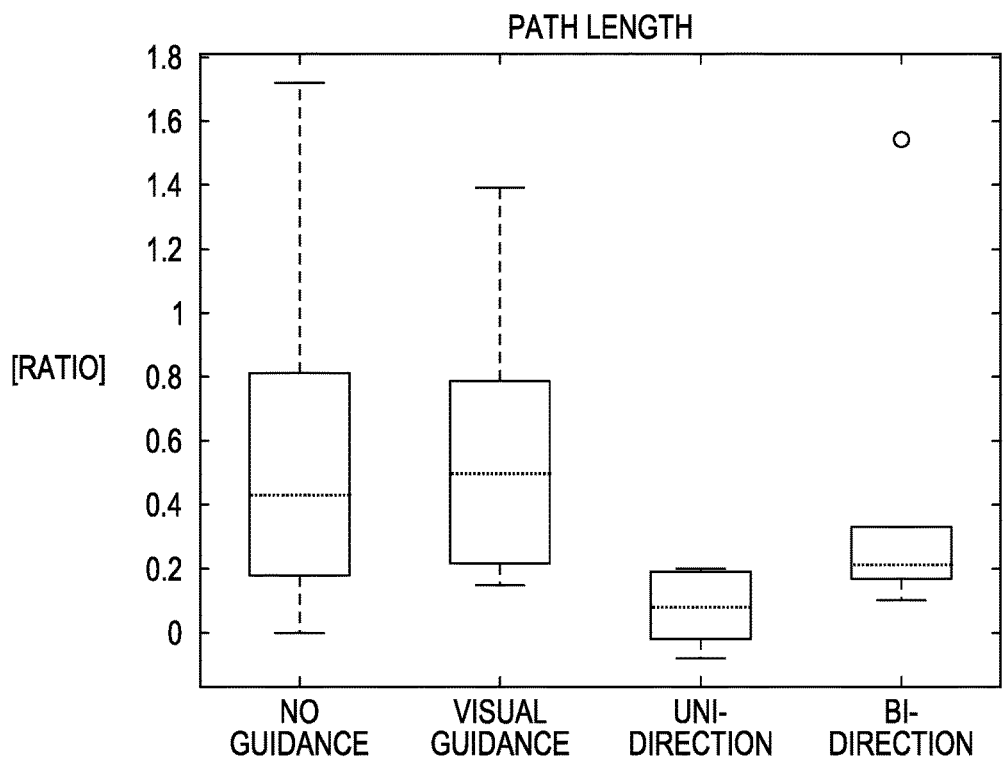
Figure 25C:
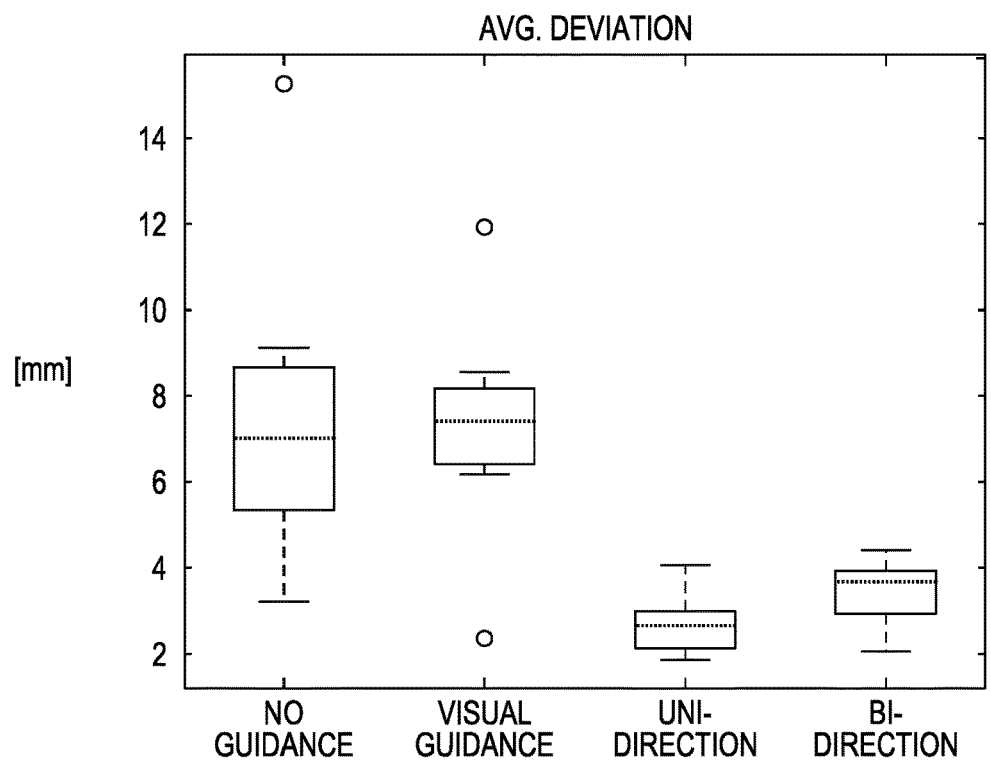
Figure 25D:
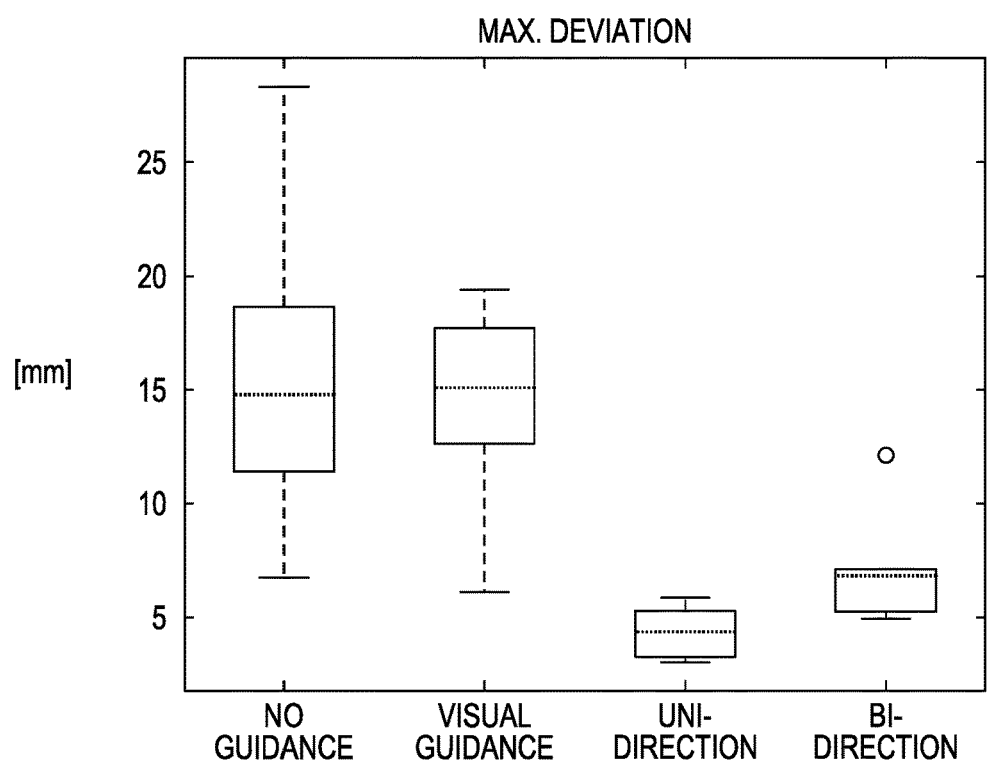

| | ← Not helpful | | | Very helpful → |
|---|---|---|---|---|
| | 0 | 1 | 2 | 3 | 4 |
| Force | 1 | | 1 | 4 | 2 |
| Visual | | 3 | 3 | | 2 | prevent the instrument from hitting the wire as shown in FIG. 24(C) and FIG. 26 (between 10 and 20 seconds). The output scaling factors were adjusted to apply a proper amount of force. Because the instrument tip was close to the wire most of the time, the output scaling factor ($G_{attr}^{ins}$) for the insertion axis kept increasing and finally reached the maximum value. Unlike depicted in FIG. 26, a tester could perform well as shown in FIG. 24(D) and FIG. 27 (i.e., maintain the reasonable distance between the instrument tip and the wire to avoid hitting the wire). Therefore, the controllers could minimize the amount of the attractive force to provide much more control authority to the tester.

Figure 28A:
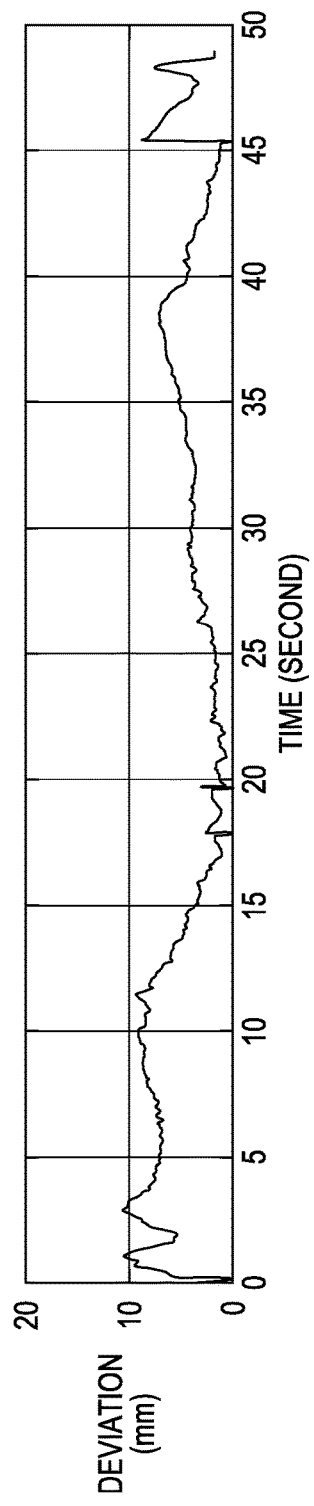
FIG. 28(A) shows the deviation from the recommended path for an example of a subjectively evaluated weak force.
Figure 28B:
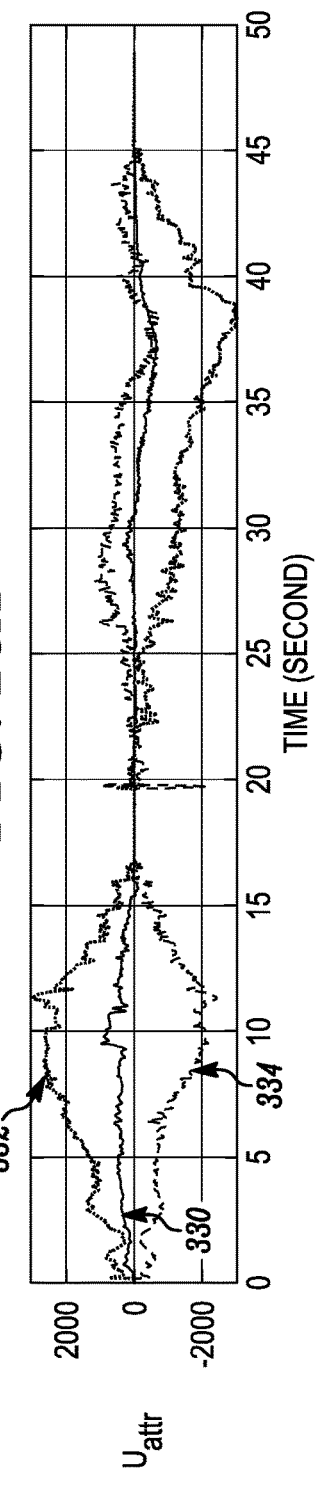
FIG. 28(B) shows the control outputs for the attractive force.
Figure 28C:
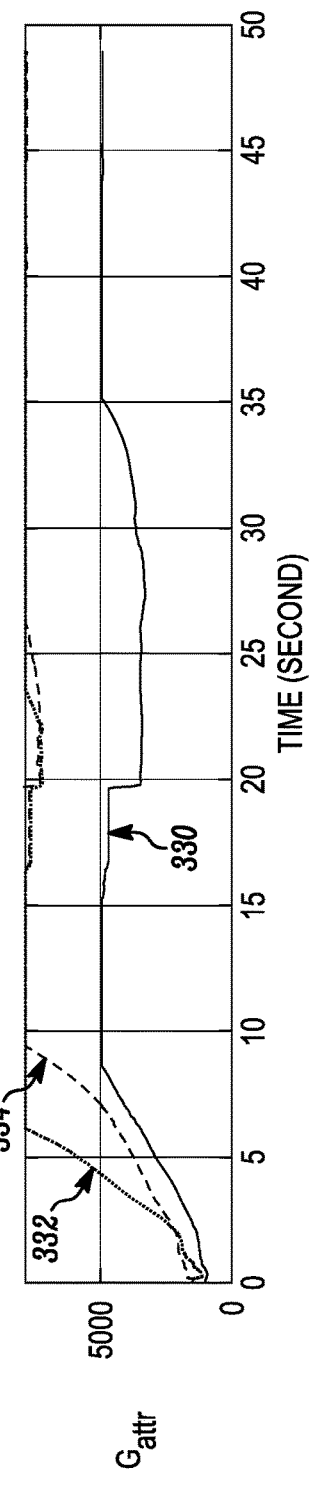
FIG. 28(C) shows the output scaling factors that are used.

The subjective evaluation results to verify the force sensitivity are presented in Table 3 (where 0 means not at all, 1: very weak, 2: weak, 3: moderate, 4: strong, and 5: very strong). Most testers reported that the amount of guidance force was reasonable enough for both force guidance types. Only one tester reported that he could not sense any force while performing. This tester might have needed much stronger force. FIG. 28 illustrates the overall performance of force guidance type 2 for this tester. All the output scaling factors already reached the maximum values around 10 seconds. Therefore, the controllers could not generate much more force. However, this tester could eventually complete the task (he could not complete it without the force navigation, which further confirms the utility of our approach for novice learners).

Table 4 (where 0: not helpful, 1: confusing, 2: moderate, 3: helpful, and 4: very helpful) shows subjective evaluation about the guidance methods. Most testers reported that the force guidance was helpful. This subjective result matches with the objective evaluation results. However, some testers reported that the visual guidance made them confused. This also matches the objective evaluation result.

CONCLUSION

The objective and subjective evaluations based on the initial test results indicate that the adaptive force guidance system is beneficial for the surgical skills training and meets the design objectives. Due to using the hand-on interface, it was challenging to restrict a non-preferred motion completely (i.e., "hard virtual fixturing"). However, the guidance system described herein has adaptive features to assist a trainee effectively by considering different force sensitivity and proficiency levels.

While a trainee performs a training task, this guidance system could provide instant feedback based on the user's live performance. In some embodiments a decision process may be employed to consider the learning curves of trainees. For instance, an expert level trainee will have full control authorities most of time even though he or she could still make small mistakes. Clearly, the guidance system will assist a novice trainee more actively to enhance the training experience. Such a decision process can be incorporated within the controllers to support this feature.

According to the results, the force guidance system was not helpful in assisting a trainee to maneuver a grasper. To enhance the guidance system various guidance methods such as visual, audio, and force may be combined. In this case, human factors (e.g., cognitive aspects) may also be taken into account as well.

An intelligent guidance system to substitute for human instructors by providing active guidance can not only enhance surgical training procedures for manual skills acquisition but it is anticipated that it will also result in better surgical outcomes and higher patient safety. Also, the controllers described herein can be used for other human-machine interaction applications and skills training devices and are not limited to the applications described herein Various embodiments described herein may be described in the general context of method steps or processes, which may be implemented in one embodiment by a computer program product, embodied in, e.g., a non-transitory computer-readable memory, including computer-executable instructions, such as program code, executed by computers in networked environments. A computer-readable memory may include removable and non-removable storage devices including, but not limited to, Read Only Memory (ROM), Random Access Memory (RAM), compact discs (CDs), digital versatile discs (DVD), etc. Generally, program modules may include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

A computer program product can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

The various embodiments described herein may be implemented in various environments. Such environments and related applications may be specially constructed for performing the various processes and operations according to the disclosed embodiments or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the disclosed embodiments, or it may be more convenient to construct a specialized apparatus or system to perform the required methods and techniques. In some cases the environments in which various embodiments described herein are implemented may employ machine-learning and/or artificial intelligence techniques to perform the required methods and techniques.

The above examples and disclosure are intended to be illustrative and not exhaustive. These examples and description will suggest many variations and alternatives to one of ordinary skill in this art. For instance, while the examples described above has illustrated the systems and techniques described herein as being applicable to measurements associated with the esophagus, more generally these systems and techniques are equally applicable to any portion of the gastrointestinal tract. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. An adaptive force guidance system for surgical training, comprising:
   a hands-on physical interface that includes a fixture supporting an actuator-controllable surgical instrument for performing a surgical training task on a physical reality training arrangement using the actuator-controllable surgical instrument, the hands-on physical interface further including at least one sensor for receiving task performance data;
   a processor configured to:
      generate or acquire a surgical training task that includes a sequence of actions to be performed by a user of the actuator-controllable surgical instrument for performing a surgical training task on the physical reality training arrangement, each action in the sequence of actions being associated with guidance geometry specifying a recommended path to be traversed to perform the action;
      while each action is being performed by the user of the actuator-controllable surgical instrument as part of the surgical training task, receive task performance data reflecting an amount by which the action being performed by the user causes a deviation from the recommended path; and
      while each action is being performed by the user of the actuator-controllable surgical instrument, cause an adaptive feedback force to be applied to the actuator-controllable surgical instrument based at least in part on the task performance data that is received, the adaptive feedback force causing a reduction in the deviation from the recommended path.

2. The system of claim 1, wherein a magnitude of the adaptive feedback force that is applied is determined by a control gain, the processor being further configured to adjust the control gain based at least in part on a magnitude of the deviation.

3. The system of claim 2, wherein the processor is further configured to increase the magnitude of the control gain as the magnitude of the deviation increases and subsequently decrease the magnitude of the control gain as the user properly manipulates the actuator-controllable surgical instrument in accordance with the guidance geometry.

4. The system of claim 2, wherein the processor is further configured to adjust the control gain based at least in part on an evaluation of past user performance data when performing previous actions in the surgical training task such that the user has more control authority when the past user performance data indicates greater proficiency and has less control authority when the past user performance data indicates less proficiency.

5. The system of claim 2, wherein the processor is further configured to adjust the control gain based at least in part on an evaluation of historical training data of the user from previous training sessions such that the user has more control authority when the evaluation indicates greater proficiency and has less control authority when the evaluation indicates less proficiency.

6. The system of claim 1, wherein the processor is further configured to adjust a rate at which guidance intervention is provided based at least in part on an evaluation of past user performance data when performing previous actions in the surgical training task such that the user has more control authority when the past user performance data indicates greater proficiency and has less control authority when the past user performance data indicates less proficiency.

7. The system of claim 6, wherein the guidance intervention that is provided is selected from the group comprising a frequency at which adaptive feedback force intervention is applied, a rate at which visual guidance provided, and a rate at which audio guidance is provided.

8. The system of claim 2, wherein the task performance data further reflects one or more characteristics of the actuator-controllable surgical instrument as the user is performing the action, the processor being further configured to adjust the control gain based at least in part on the one or more characteristics.

9. The system of claim 8, wherein the one or more characteristics are selected from the group comprising a direction in which a tip of the actuator-controllable surgical instrument is moving while the user performs the action and a speed at which the actuator-controllable surgical instrument is moving while performing the action.

10. The system of claim 1, wherein the adaptive feedback force includes an attractive adaptive feedback force.

11. The system of claim 1, wherein the processor is further configured to generate performance evaluation data assessing user proficiency at a completion of the training task.

12. The system of claim 1, wherein the adaptive feedback force includes an assistive adaptive feedback force.

* * * * *